(12) United States Patent
Kitahara

(10) Patent No.: US 9,427,214 B2
(45) Date of Patent: Aug. 30, 2016

(54) MEDICAL APPARATUS

(71) Applicant: OLYMPUS CORPORATION, Tokyo (JP)

(72) Inventor: Toshihiro Kitahara, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/982,922

(22) Filed: Dec. 29, 2015

(65) Prior Publication Data

US 2016/0128676 A1 May 12, 2016

Related U.S. Application Data

(63) Continuation of application No. PCT/JP2014/077290, filed on Oct. 14, 2014.

(30) Foreign Application Priority Data

Dec. 16, 2013 (JP) .................................. 2013-259181

(51) Int. Cl.
*A61B 8/00* (2006.01)
*A61B 8/12* (2006.01)

(52) U.S. Cl.
CPC .. *A61B 8/56* (2013.01); *A61B 8/12* (2013.01)

(58) Field of Classification Search
CPC ....................................................... A61B 8/56
USPC ........................................................ 307/139
See application file for complete search history.

(56) References Cited

U.S. PATENT DOCUMENTS

| 4,913,984 A | 4/1990 | Shimizu |  |
|---|---|---|---|
| 2005/0075545 A1* | 4/2005 | Honda | A61B 1/00039 600/301 |
| 2012/0012638 A1* | 1/2012 | Huang | A61B 17/07207 227/176.1 |

FOREIGN PATENT DOCUMENTS

| JP | H02-056850 A | 2/1990 |
| JP | H09-201366 A | 8/1997 |
| JP | 2000-325292 A | 11/2000 |

OTHER PUBLICATIONS

International Search Report dated Jan. 13, 2015 issued in International Patent Application No. PCT/JP2014/077290.

* cited by examiner

*Primary Examiner* — Kenneth B Wells
*Assistant Examiner* — James P Evans
(74) *Attorney, Agent, or Firm* — Scully, Scott, Murphy & Presser, PC

(57) ABSTRACT

An ultrasound observation apparatus includes: a main power-supply button that operates an internal power-supply unit to be turned on/off as a result of depression of the main power-supply button; a moving member capable of moving substantially in parallel to a direction of the depression of the main power-supply button in conjunction with the depression of the main power-supply button; an internal power-supply switch provided at the power-supply unit so as to be in contact with the moving member, the internal power-supply switch switching the power-supply unit on/off by being depressed along with movement of the moving member; and a movement amount adjusting mechanism that upon the depression of the main power-supply button, if an amount of movement of the main power-supply button exceeds a predetermined movement amount, adjusts an amount of movement of a contact portion of the moving member.

15 Claims, 18 Drawing Sheets

US 9,427,214 B2

MEDICAL APPARATUS

CROSS REFERENCE TO RELATED APPLICATION

This application is a continuation application of PCT/JP2014/077290 filed on Oct. 14, 2014 and claims benefit of Japanese Application No. 2013-259181 filed in Japan on Dec. 16, 2013, the entire contents of which are incorporated herein by this reference.

BACKGROUND OF THE INVENTION

1. Field of the Invention

The present invention relates to a medical apparatus, and particularly relates to a medical apparatus in which a power-supply button is provided at an outer face of the medical apparatus and an operation of the power-supply button is transmitted to a power-supply switch of a power-supply unit inside a housing, whereby the power-supply unit is turned on/off.

2. Description of the Related Art

In recent years, medical apparatuses using electronic circuits such as ultrasound diagnostic apparatuses and video processors for endoscopes have widely been in practical use. Such medical apparatuses are electronic devices equipped with, e.g., semiconductor integrated circuits, and include an internal power-supply section for driving the electronic circuits.

The power-supply section is unitized from the perspectives such as noise prevention and current leakage prevention. Also, from the perspective of layout, the internal power-supply section is often installed on the back side in the inside of the medical apparatus. For example, in the case of the ultrasound diagnostic apparatuses, a connector for an ultrasound endoscope is disposed at a front panel on a front face of the housing and thus the internal power-supply section is installed on the back side in the inside of the housing. Also, a power-supply button of the medical apparatus is disposed at the front panel of the housing.

In the medical apparatuses, where the internal power-supply section is disposed on the back side in the inside of the housing, a mechanism for operating a power-supply button of the internal power-supply section inside the housing in conjunction with an operation of the power-supply button at the front panel is required. For example, Japanese Patent Application Laid-Open Publication Nos. 9-201366 and 2000-325292 each disclose a configuration in which upon a power-supply button at a front panel of a medical apparatus being turned on/off, a switch of an internal power-supply section is also turned on/off using a connecting rod.

SUMMARY OF THE INVENTION

A medical apparatus according to an aspect of the present invention is a medical apparatus including a housing, the medical apparatus including: a power-supply section disposed in an inside of the medical apparatus; a power-supply button provided at an outer face of the housing, the power-supply button operating the power-supply section to be turned on/off as a result of depression of the power-supply button; a moving member capable of moving in conjunction with the depression of the power-supply button; a switch provided at the power-supply section so as to be in contact with the moving member, the switch switching the power-supply section on/off as a result of the switch being depressed along with movement of the moving member; and a movement amount adjusting mechanism that upon the depression of the power-supply button, if an amount of movement of the power-supply button exceeds a predetermined movement amount, adjusts an amount of movement of a contact portion of the moving member, the contact portion being in contact with the switch, so that the amount of movement of the contact portion of the moving member, the contact portion being in contact with the switch, becomes smaller relative to the amount of movement of the power-supply button.

DETAILED DESCRIPTION OF THE PREFERRED EMBODIMENTS

Embodiments of the present invention will be described below with reference to the drawings.

First Embodiment

Configuration of Ultrasound Observation Apparatus

Figure 1:
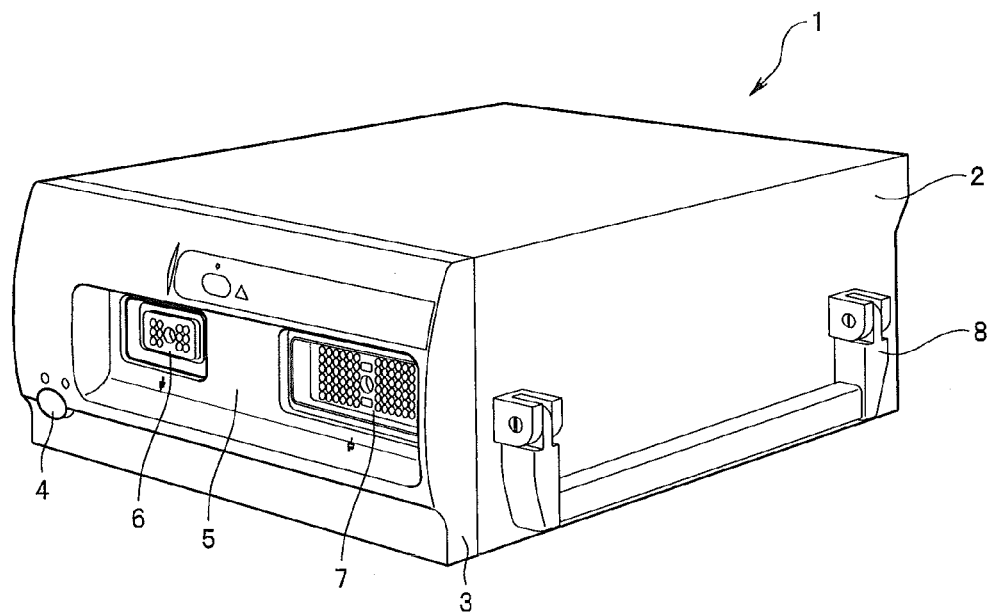
FIG. 1 is a diagram of an outer appearance of an ultrasound observation apparatus according to a first embodiment of the present invention.
Figure 2:
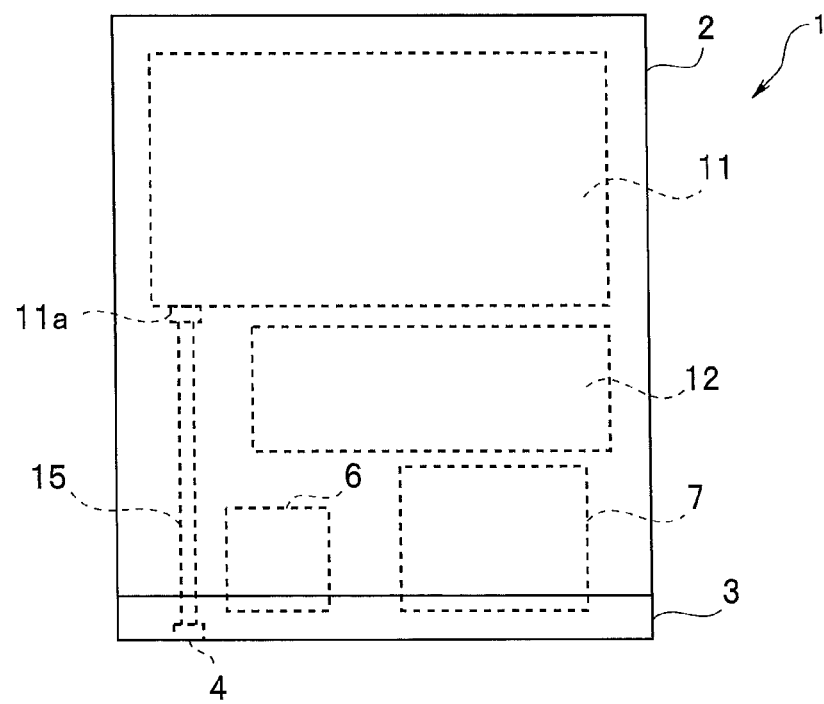
FIG. 2 is a plan view illustrating a layout of the inside of the ultrasound observation apparatus according to the first embodiment.

FIG. 1 is a diagram of an outer appearance of an ultrasound observation apparatus according to the present embodiment. FIG. 2 is a plan view illustrating a layout of the inside of the ultrasound observation apparatus according to the present embodiment. FIG. 1 is a perspective view of the horizontally-placed ultrasound observation apparatus as viewed from the upper diagonal right side toward a front panel.

In the present embodiment, as an example of medical apparatuses, an ultrasound observation apparatus will be described. An ultrasound observation apparatus is a component of an ultrasound endoscope system. An ultrasound endoscope system includes, for example, an ultrasound endoscope, an endoscope processor and a light source apparatus in addition to an ultrasound observation apparatus. The ultrasound observation apparatus performs processing for generating an ultrasound observation image from an ultrasound image signal obtained by the ultrasound endoscope and displaying the image on a monitor.

An ultrasound observation apparatus 1, which includes a plurality of circuit sections inside a housing 2, has a rough rectangular parallelepiped outer shape. At a front panel 3 of the ultrasound observation apparatus 1, a power-supply button 4, and two connection portions, apparatus-side connector units 6 and 7, disposed side by side on an apparatus-side connector disposition surface 5 formed in the front panel 3, to which two different types of connectors are to be connected, are provided.

An apparatus-side unit connector 6 disposed on the left side as viewed facing the front panel 3 in the apparatus-side connector disposition surface 5 is, for example, a 50-core plug connector or socket to be paired with an ultrasound connector for a mechanic-scanning ultrasound medical device. The apparatus-side connector unit 7 disposed on the right side as viewed facing the front panel 3 is, for example, a 150-core plug connector or socket to be paired with an ultrasound connector for an electronic-scanning ultrasound medical device. Note that on each of opposite side faces of the housing 2, a handle portion 8 is provided.

As illustrated in FIG. 2, inside the housing 2, a power-supply unit 11, the apparatus-side connector units 6 and 7, and a substrate 12 are provided. The power-supply unit 11 is a power-supply section disposed in the inside of the ultrasound observation apparatus 1, which is a medical apparatus, and is disposed on the rear side of the housing 2. The apparatus-side connector unit 6 is arranged on the front side of the housing 2 in such a manner that the surface to which an ultrasound connector (not illustrated) of a mechanic-scanning ultrasound medical device is to be connected is disposed in the front panel 3. The apparatus-side connector unit 7 is disposed on the front side of the housing 2 in such a manner that the surface to which an ultrasound connector (not illustrated) of an electronic-scanning ultrasound medical device is to be connected is disposed in the front panel 3.

A substrate 12 with various electronic circuits mounted is disposed between the apparatus-side connector units 6 and 7 disposed on the front side of the housing 2 and the power-supply unit 11 disposed on the rear side of the housing 2. The housing 2 includes a power-supply button (hereinafter referred to as "main power-supply button") 4 at a front face. A power-supply switch (hereinafter referred to as "internal power-supply switch") 11a of the power-supply unit 11 is disposed inside the housing 2 so as to face the front side of the housing 2.

A link mechanism 15 is provided between the main power-supply button 4 provided at the front face of the housing 2 and the internal power-supply switch 11a of the power-supply unit 11, which is an internal power supply, and the internal power-supply switch 11a is configured so as to operate in conjunction with operation of the main power-supply button 4. In other words, the main power-supply button 4 is a power-supply button provided at an outer face of the ultrasound observation apparatus 1, which is a medical apparatus, the power-supply button operating the power-supply unit 11 to be turned on/off as a result of depression of the main power-supply button 4. An operation of the main power-supply button 4 is transmitted to the internal power-supply switch 11a of the power-supply unit 11 inside the housing 2, whereby the power-supply unit 11 is turned on/off.

As described below, in the link mechanism 15, a biasing member for, upon application of an excessive external force to the main power-supply button 4, preventing the excessive external force from being directly applied to the internal power-supply switch 11a of the power-supply unit 11, which is an internal power supply, is provided.

(Configuration of Link Mechanism)

Figure 3:
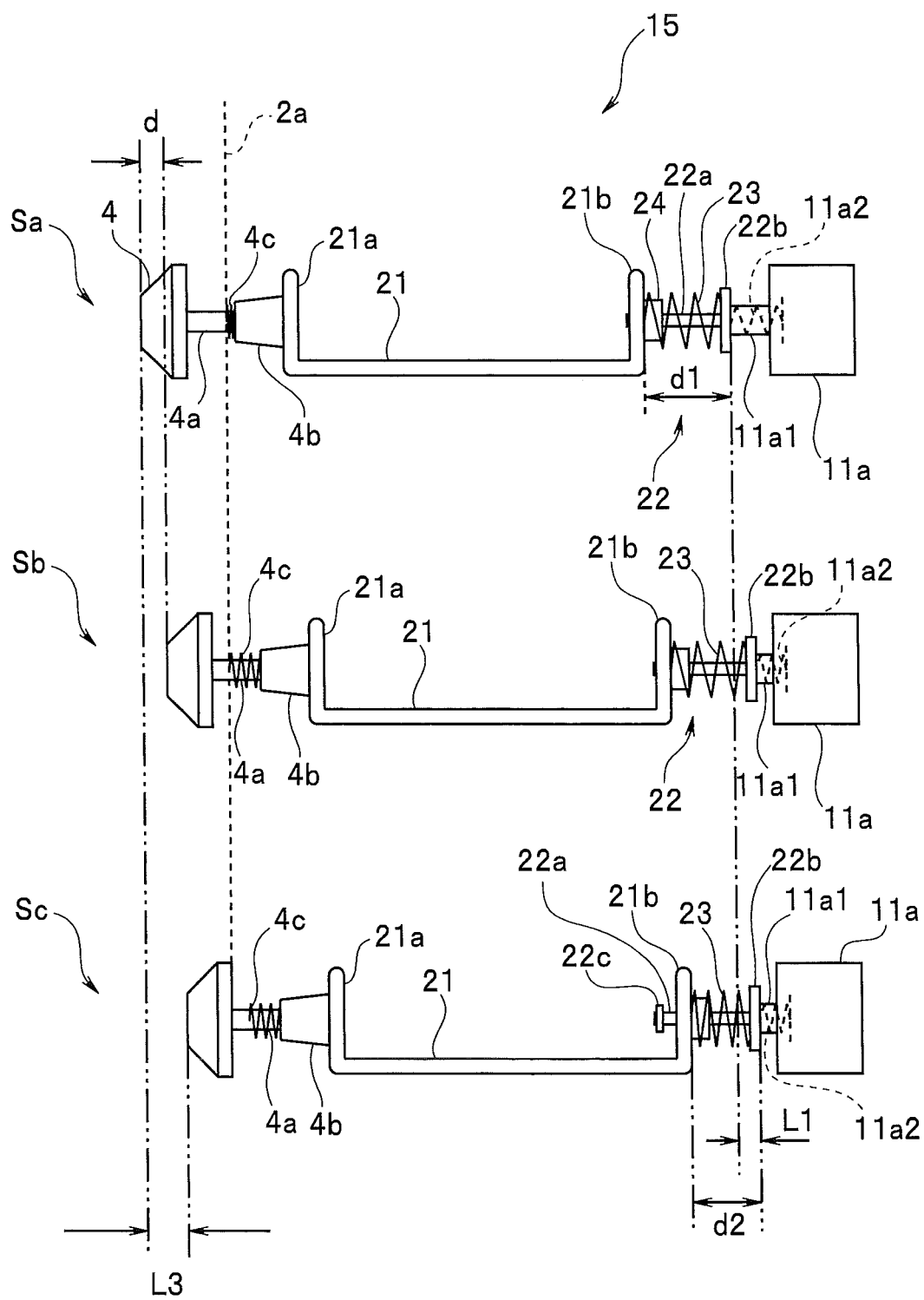
FIG. 3 is a conceptual diagram for describing motion of a link mechanism 15, according to the first embodiment.
Figure 4:
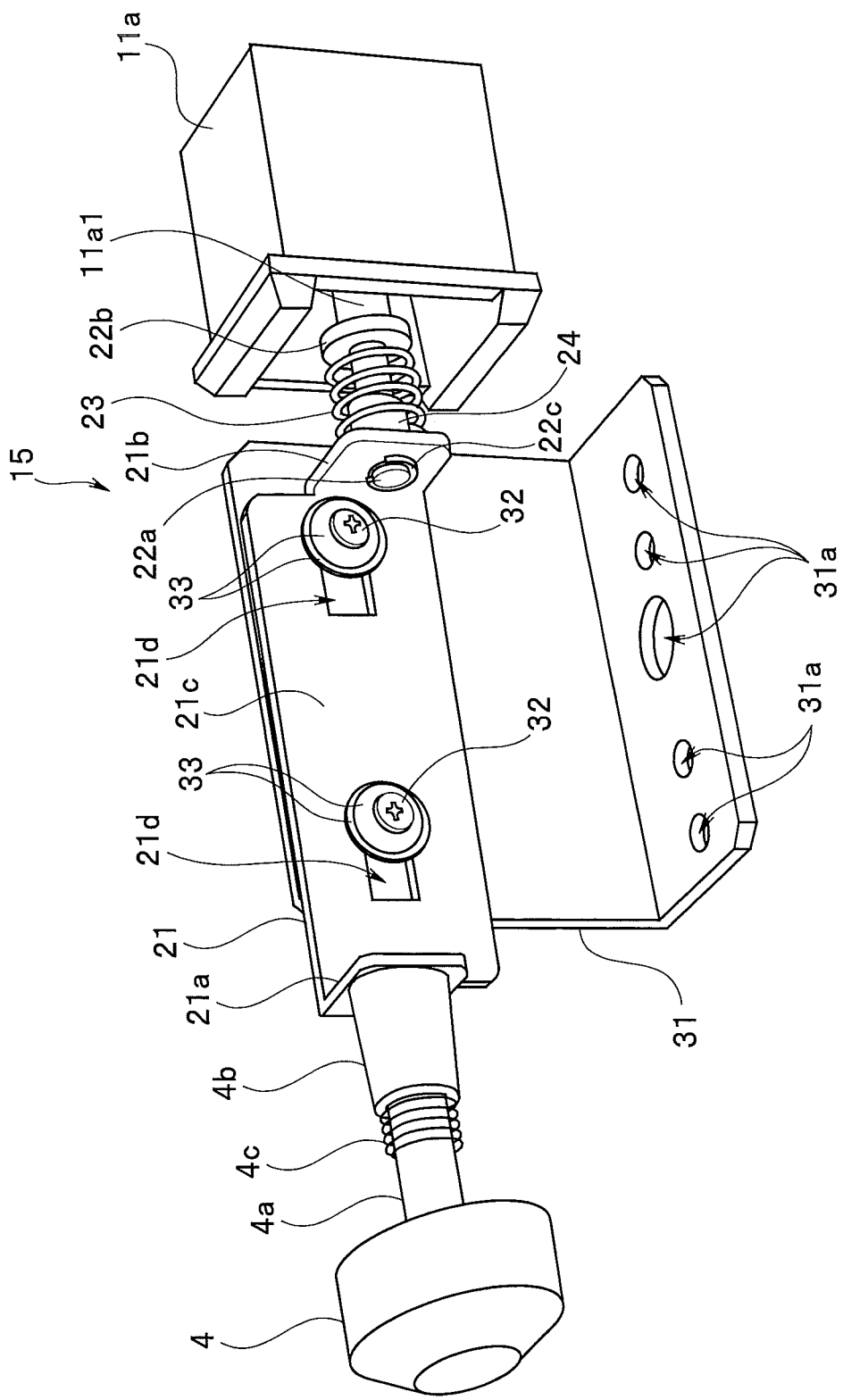
FIG. 4 is a perspective view of the link mechanism 15, according to the first embodiment.
Figure 5:
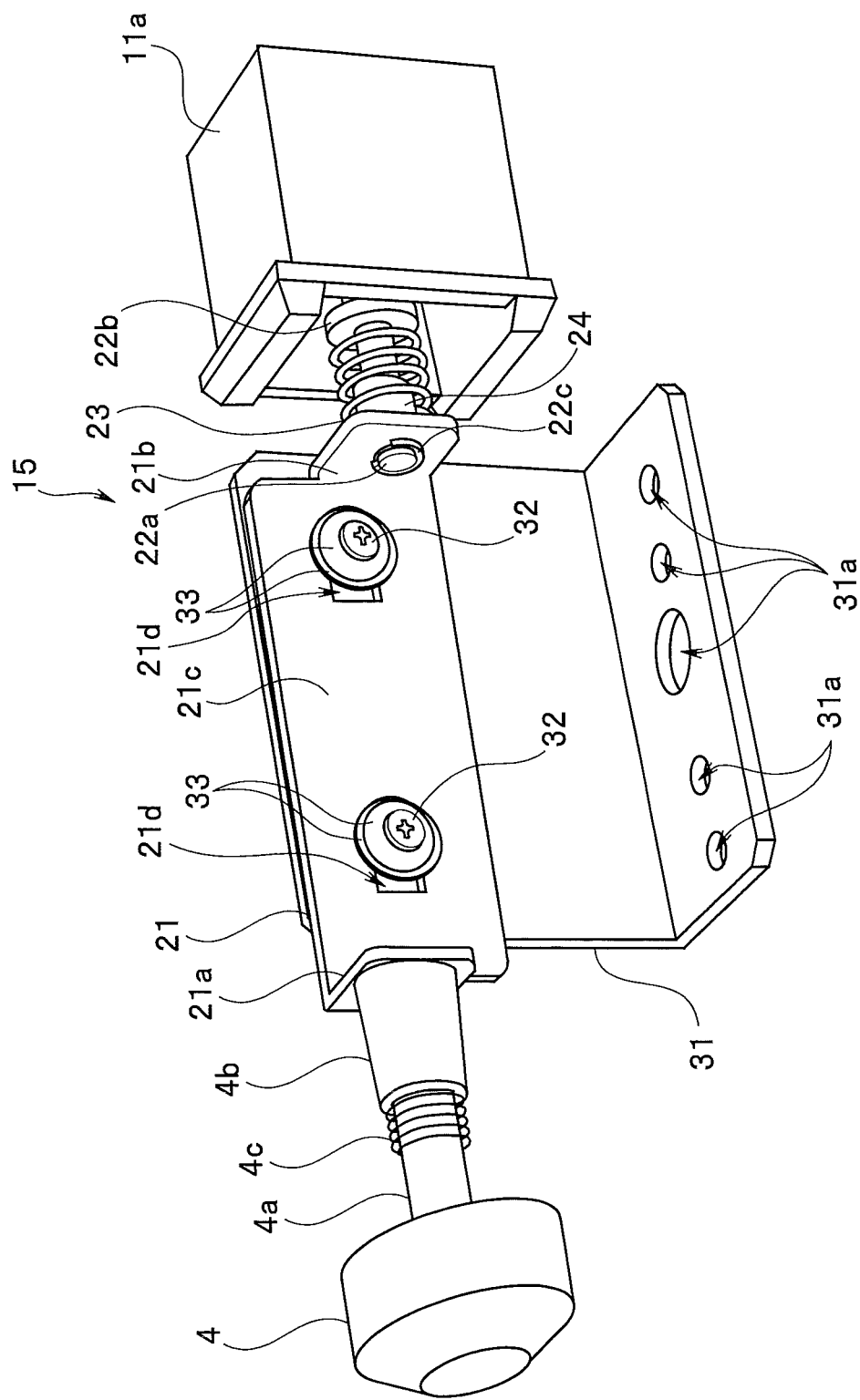
FIG. 5 is a perspective view of the link mechanism 15 when an internal power-supply switch 11a is turned on as a result of a main power-supply button 4 being pressed, according to the first embodiment.

Next, the link mechanism 15 will be described with reference to FIG. 3, which is a conceptual diagram, and FIGS. 4 to 6 each illustrating a specific configuration of members. FIG. 3 is a conceptual diagram for describing motion of the link mechanism 15. FIG. 4 is a perspective view of the link mechanism 15. FIG. 4 is an initial state in which the main power-supply button 4 is not pressed.

A proximal end portion of the main power-supply button 4 is in contact with a distal end portion of the link mechanism 15. More specifically, the main power-supply button 4 includes a shaft portion 4a extending to the proximal end side, and a switch collar 4b is fixed to a proximal end portion of the shaft portion 4a. The switch collar 4b is in contact with the distal end portion of the link mechanism 15.

A spring member 4c is provided in the main power-supply button 4, and the shaft portion 4a is inserted through the inside of the spring member 4c. The spring member 4c is provided between the housing 2 and the switch collar 4b. More specifically, a distal end portion of the spring member 4c is in contact with an inner wall 2a, and a proximal end portion of the spring member 4c is in contact with a distal end portion of the switch collar 4b. When the main power-supply button 4 is not pressed, the spring member 4c depresses the distal end portion of the switch collar 4b so as to bias the main power-supply button 4 in a direction that is opposite to a direction toward the front panel 3 side.

The internal power-supply switch 11a of the power-supply unit 11 includes a spring member 11a2 inside, and the spring member 11a2 biases an operating element 11a1 in a direction toward the front side of the power-supply unit 11 (main power-supply button 4 side). The operating element 11a1 is in contact with a proximal end portion of a moving member 22. In other words, the internal power-supply switch 11a is a switch provided at the power-supply unit 11 so as to be in contact with the proximal end portion of the moving member 22, the switch switching the power-supply unit 11 on/off as a result of the switch being depressed along with movement of the moving member 22. The internal power-supply switch 11a is configured so that when the operating element 11a1 is not pressed, the operating element 11a1 is located at a reference position (position when the operating element 11a1 is not pressed) by means of a biasing force of the spring member 11a2.

The link mechanism 15 includes a depressing member 21, a moving member 22 and a compression coil spring 23.

The depressing member 21, which is a plate-like member flexed so as to form a square-U shape and formed of, for example, a metal, includes a flexed portion 21a on the distal end side, and a flexed portion 21b on the proximal end side. In a center portion 21c of the depressing member 21, two opening portions 21d are formed.

The depressing member 21 is supported by a supporting member 31 inside the housing 2. The supporting member 31 includes a plurality of opening portions 31a for fixing the supporting member 31 to the housing 2 via screws, and is fixed to the housing 2. Furthermore, in the supporting member 31, two screw holes (not illustrated) to which shaft portions of two screws 32 inserted through the two opening portions 21d of the depressing member 21 are threadably connected are formed.

As illustrated in FIG. 4, each opening portion 21d has a shape elongated along a direction in which the depressing member 21 moves when the main power-supply button 4 is pushed in. The shaft portion of each screw 32 is threadably connected and fixed to the corresponding screw hole of the supporting member 31 via a plurality of washers 33 and the corresponding opening portion 21d in such a manner that the depressing member 21 is not fixed but is movable, so that along with an operation to push the main power-supply button 4 in, the depressing member 21 can move in a direction in which the main power-supply button 4 moves.

The flexed portion 21b on the proximal end side of the depressing member 21 is provided with the moving member 22 biased with a predetermined biasing force by the compression coil spring 23 in such a manner that the moving member 22 can move along a direction in which the main power-supply button 4 moves. The flexed portion 21a is a power-supply button contact portion, and the flexed portion 21b is a moving member disposition portion.

Upon the main power-supply button 4 being pressed, the shaft portion 4a moves toward the inside of the housing 2 and the flexed portion 21a presses to the proximal end side. The pressed depressing member 21 moves to the proximal end side, and along with the movement of the depressing member 21, the moving member 22 also moves to the proximal end side. In other words, the moving member 22 is a member capable of moving substantially in parallel to a direction of depression of the main power-supply button 4 in conjunction with the depression of the main power-supply button 4.

The moving member 22 is a member including a rod-like shaft portion 22a formed of, for example, a metal, and a disk-like spring receiving portion 22b formed on the proximal end side of the shaft portion 22a. The spring receiving portion 22b is disposed on the internal power-supply switch 11a so that the spring receiving portion 22b can press the operating element 11a1 of the internal power-supply switch 11a of the power-supply unit 11.

A retaining ring 22c is fixed on the distal end side of the shaft portion 22a. The retaining ring 22c is fitted in a circumferential groove formed in a distal end-side part of the shaft portion 22a and fixed to the shaft portion 22a. In the flexed portion 21b of the depressing member 21, a hole is formed, and a cylindrical member 24 is fixed in the hole. The shaft portion 22a of the moving member 22 is inserted through the hole of the flexed portion 21b with the shaft portion 22a inserted through the inside of the cylindrical member 24 so that the shaft portion 22a can move in an axial direction.

The compression coil spring 23 is a coiled spring member, which is an elastic member. The compression coil spring 23 is interposed in a compressed state between the flexed portion 21b and the spring receiving portion 22b with the shaft portion 22a of the moving member 22 inserted through the inside of the compression coil spring 23. The compression coil spring 23 can be provided in a compressed state between the flexed portion 21b and the spring receiving portion 22b by the cylindrical member 24 with the shaft portion 22a inserted through the inside of the cylindrical member 24 being inserted into the coiled compression coil spring 23 and the retaining ring 22c being attached to the shaft portion 22a with the compression coil spring 23, which is a spring member, compressed.

(Operation of Link Mechanism)

Next, operation of the link mechanism 15 will be described.

State Sa in FIG. 3, which corresponds to the state in FIG. 4, indicates an initial state of the main power-supply button 4, the depressing member 21, the moving member 22 and the internal power-supply switch 11a when the main power-supply button 4 in the housing 2 is not pressed. Upon the main power-supply button 4 being pressed, the state of the link mechanism 15 varies from state Sa to state Sb. Upon the main power-supply button 4 being pushed in and moving toward the inside of the housing 2, the depressing member 21 moves according to the movement of the main power-supply button 4.

State Sb in FIG. 3 indicates a state of the main power-supply button 4, depressing member 21, the moving member 22 and the internal power-supply switch 11a when the main power-supply button 4 of the housing 2 is pushed in, whereby the internal power-supply switch 11a is turned on. FIG. 5 is a perspective view of the link mechanism 15 when the internal power-supply switch 11a is turned on as a result of the main power-supply button 4 being pressed.

An amount of force of the compression coil spring 23 (that is, an amount of force of the compressed compression coil spring 23 biasing the depressing member 21 to the main power-supply button 4 side) P2 is set or adjusted to an amount that is equal or exceeding a force amount P1 required to press the main power-supply button 4 to turn on the internal power-supply switch 11a. The compression coil spring 23 is compressed and shrinks upon application of a force exceeding a force amount P2 to the compression coil spring 23.

Also, for the internal power-supply switch 11a, a permissible force amount P3, which is a permissible withstanding force, is set as a design value. Therefore, upon application of an amount of force exceeding the permissible force amount P3 under a predetermined condition to the internal power-supply switch 11a, the internal power-supply switch 11a may break. The amount of force of the compression coil spring 23 (that is the amount of force of the compressed compression coil spring 23 biasing the depressing member 21 to the main power-supply button 4 side) P2 is set to be equal to or below the permissible force amount P3.

In other words, P1, P2 and P3 are set so as to satisfy Expression (1) below:

$$P3 \geq P1 - P2 \quad (1)$$

As a result of P1, P2 and P3 satisfying the condition in Expression (1), the internal power-supply switch 11a is prevented from breaking when the internal power-supply switch 11a is turned on/off.

Here, for example, assuming that an impact force when a hard ball collides with the main power-supply button 4 in a hard ball dropping test prescribed in, e.g., standards or the like, where g is a gravitational acceleration, L is a length of pendulum (=1 m) and θ is an angle relative to a vertical direction (=90 degrees), if a speed of the steel ball colliding with the main power-supply button 4 is 4.43 m/s and a weight m of the steel ball is 0.5 kg, an amount of momentum in the collision is 2.22 Ns.

Since a time period of collision is from 0.01 seconds to 0.1 seconds according to a test conducted by the applicant in the past, if the time period, which is described above, is 0.01 seconds, the force amount P1 is 220 N, and if the time period is 0.1 seconds, the force amount P1 is 22.2 N. In consideration of errors, it can be assumed that the force amount is 250 N at the maximum. Therefore, the force amount is no more than 250 N.

Since the permissible force amount P3 for the internal power-supply switch 11a is, for example, 150 N, the internal power-supply switch 11a is prevented from breaking if buffering can be provided so that the time period during which an impact force is applied to the internal power-supply switch 11a becomes no less than 0.0148 seconds.

Upon a user pressing the main power-supply button 4 to turn on power of the medical device 1, the depressing member 21 moves by an amount that is the same as an amount of the movement of the main power-supply button 4. This is because since the force amount P2 (that is, the biasing force) of the compression coil spring 23 is equal to or exceeds the force amount P1 of the main power-supply button 4 being pressed, the compression coil spring 23 does not shrink. Therefore, upon the main power-supply button 4 being pressed, the operating element 11a1 of the internal power-supply switch 11a is pushed in by the depressing member 21, whereby the internal power-supply switch 11a is turned on.

The amount of movement of the main power-supply button 4 at this stage is a predetermined amount of distance d from a position where movement of the depressing member 21 starts to a position where the movement of the depressing member 21 stops, which is a position where the internal power-supply switch 11a is turned on and the operating element 11a1 of the internal power-supply switch 11a cannot be pressed any further.

Also, upon the pressing of the main power-supply button 4 being stopped, the operating element 11a1 is urged to return to an original position (that is, a position where the operating element 11a1 is not pressed) by a biasing force the internal power-supply switch 11a has, and thus the depressing member 21 presses the main power-supply button 4 back. As a result, the main power-supply button 4, etc., return from state Sb in FIG. 3 (FIG. 5) to state Sa (FIG. 4).

Upon application of a large impact force to the main power-supply button 4 as a result of something crashing into the main power-supply button 4, the main power-supply button 4 further moves toward the inside of the housing 2 beyond the position indicated in state Sb. Then, upon movement of the main power-supply button 4 to a position such as indicated in state Sc, the depressing member 21 simultaneously moves in a direction that is the same as a direction of the movement of the main power-supply button 4.

In other words, when an excessively-large force is applied to the main power-supply button 4, the main power-supply button 4 and the depressing member 21 move beyond the aforementioned predetermined amount of distance d.

Figure 6:
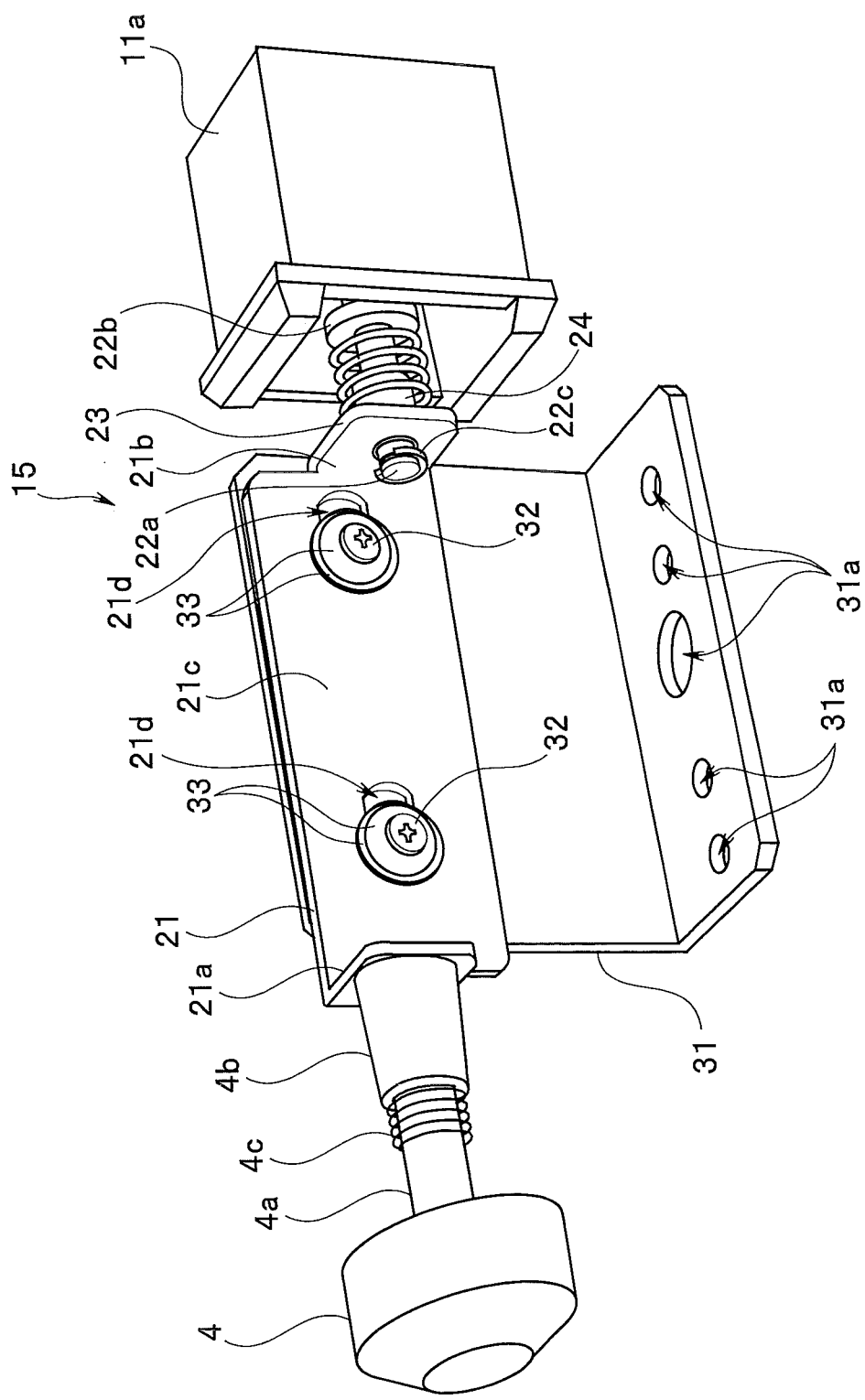
FIG. 6 is a perspective view of the link mechanism 15 when an excessively-large force applied to the main power-supply button 4 is buffered, according to the first embodiment.

FIG. 6 is a perspective view of the link mechanism 15 when an excessively-large force applied to the main power-supply button 4 is buffered.

The link mechanism 15 is configured so that when a large force is applied to the main power-supply button 4, the compression coil spring 23 absorbs the force to prevent a force exceeding the permissible force amount P3, which is a permissible withstanding force, from being applied to the internal power-supply switch 11a.

Regarding the amounts of movement of the respective members when the state varies from Sa to Sc, first, when the state varies from Sa to Sb, the state varies from a state in which the operating element 11a1 of the internal power-supply switch 11a is not pressed to a state in which the operating element 11a1 is pushed in and the internal power-supply switch 11a is turned on.

During variation from state Sb to state Sc, the compression coil spring 23 is compressed in the axial direction. As illustrated in FIG. 3, where d1 is a length from a proximal end face of the flexed portion 21b of the depressing member 21 to a proximal end face of the spring receiving portion 22b of the moving member 22 in state Sa and d2 is the length from the proximal end face of the flexed portion 21b of the depressing member 21 to the proximal end face of the spring receiving portion 22b of the moving member 22 in state Sc, a compression amount L2 of the compression coil spring 23 can be expressed by Expression (2) below.

$$L2 = d1 - d2 \quad (2)$$

Where L1 is a permissible movement amount of the operating element 11a1 of the internal power-supply switch 11a, L2 is the compression amount of the compression coil spring 23 and L3 is an amount of movement of the main power-supply button 4, L1, L2 and L3 are set so as to satisfy Expression (3) below.

$$L2 \geq L3 - L1 \quad (3)$$

As a result of L1, L2 and L3 satisfying Expression (3), the internal power-supply switch 11a is prevented from breaking when the main power-supply button 4 is pressed.

The compression amount L2 of the compression coil spring 23 can be regarded as an amount of adjustment of movement of the moving member 22.

In state Sb, the operating element 11a1 of the internal power-supply switch 11a is pushed in furthest and cannot be pushed in any further.

If the main power-supply button 4 is further pushed in toward the inside of the housing 2 beyond the position indicated in state Sb because of, e.g., an external impact, the depressing member 21 is further moved toward the inside of the housing 2 by the switch collar 4b of the main power-supply button 4 beyond the aforementioned predetermined amount of distance d.

The state Sc indicates a state in which the main power-supply button 4 is further pushed in toward the inside of the housing 2 beyond the position indicated in state Sb.

During normal operation, the internal power-supply switch 11a does not break as long as the movement amount L3 of the main power-supply button 4 is equal to or below the permissible movement amount L1 of the internal power-supply switch 11a. For example, if the permissible movement amount L1 of the internal power-supply switch 11a is 3 mm and the movement amount L3 of the main power-supply button 4 is 3 mm or less, there is no possibility of breakage of the internal power-supply switch 11a.

However, if the movement amount L3 of the main power-supply button 4 exceeds the permissible movement amount L1 of the internal power-supply switch 11a as a result of, e.g., something crashing into the main power-supply button 4, the internal power-supply switch 11a may break as a result of the main power-supply button 4 being pressed. For example, if the permissible movement amount L1 of the internal power-supply switch 11a is 3 mm and the movement amount L3 of the main power-supply button 4 is 5 mm, the additional movement amount of 2 mm is added to the internal power-supply switch 11a, which may result in breakage of the internal power-supply switch 11a.

Therefore, upon the depressing member 21 moving toward the inside of the housing 2 beyond the aforementioned predetermined amount of distance d, the link mechanism 15 prevents breakage of the internal power-supply switch 11a by the compression coil spring 23 being compressed to absorb the excessive movement amount. For example, in the above example, even if the movement amount L3 of the main power-supply button 4 is 5 mm, the compression coil spring 23 is compressed to prevent the movement amount of the operating element 11a1 of the internal power-supply switch 11a from exceeding the permissible movement amount L1.

In other words, the compression coil spring 23 provides a movement amount adjusting mechanism that upon depression of the main power-supply button 4, if an amount of movement of the main power-supply button 4 exceeds a predetermined movement amount d, adjusts an amount of movement of the proximal end portion of the moving member 22 so that an amount of movement of a contact portion of the moving member 22, the contact portion being in contact with the internal power-supply switch 11a (proximal end portion of the moving member 22), becomes smaller relative to the amount of movement of the main power-supply button 4. In other words, if the movement amount L3 of the main power-supply button 4 exceeds a predetermined amount, the movement amount adjusting mechanism allows the compression coil spring 23 to be compressed against the biasing force of the compression coil spring 23, whereby the amount of movement of the moving member 22 is adjusted.

Therefore, even upon movement of the main power-supply button 4 causing the internal power-supply switch 11a to move by the permissible movement amount L1 or more as a result of application of an impact force to the main power-supply button 4, the amount of force applied to the main power-supply button 4 is buffered by the compression coil spring 23 in the link mechanism 15. As a result, the internal power-supply switch 11a is prevented from being subject to an amount of force exceeding the permissible force amount P3, whereby the internal power-supply switch 11a is prevented from breakage.

As described above, the present embodiment enables provision of a medical apparatus capable of preventing breakage of a power-supply button of an internal power-supply section even if an excessive external force is applied to a power-supply button provided at a housing of the medical apparatus.

Second Embodiment

Although in the first embodiment, the link mechanism uses the compression coil spring 23 to prevent the internal power-supply switch 11a from being subject to an amount of force exceeding the permissible force amount P3, in the present embodiment, a link mechanism uses a plate spring.

In the below description, components that are the same as those of the first embodiment are provided with reference numerals that are the same as those of the first embodiment, and description of such components are omitted.

Figure 7:
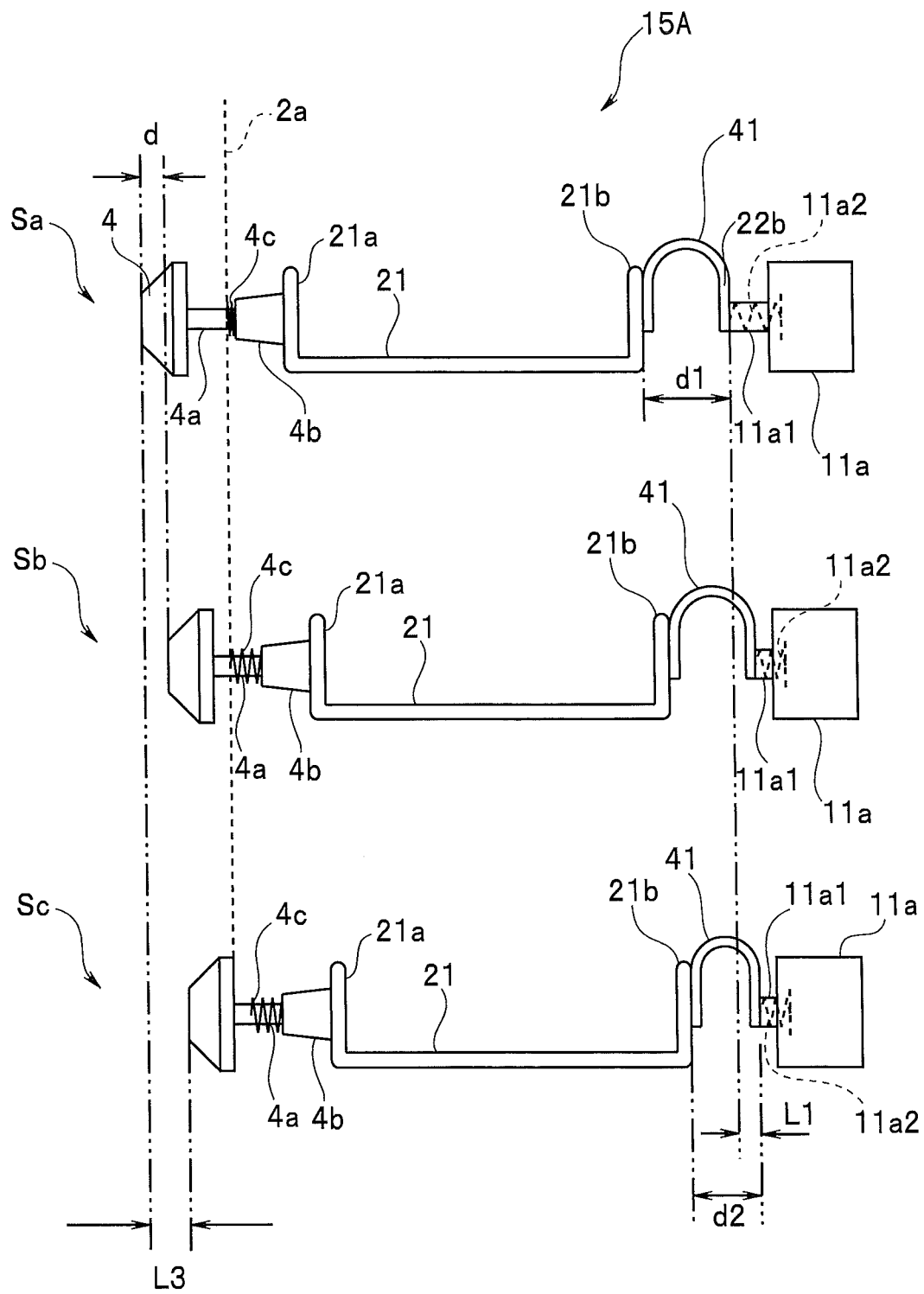
FIG. 7 is a conceptual diagram for describing motion of a link mechanism 15A according to a second embodiment.
Figure 8:
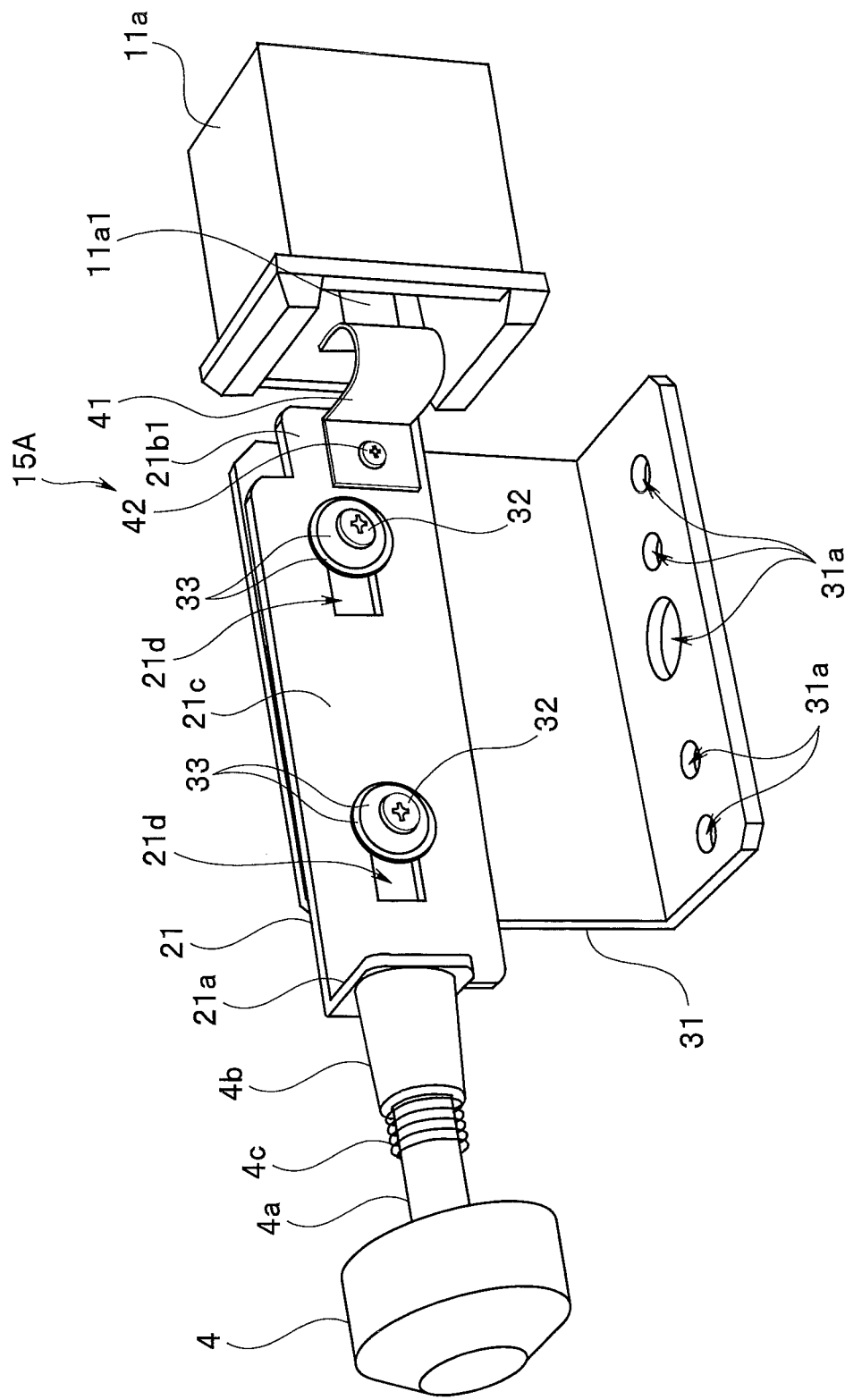
FIG. 8 is a perspective view of the link mechanism 15A according to the second embodiment.
Figure 9:
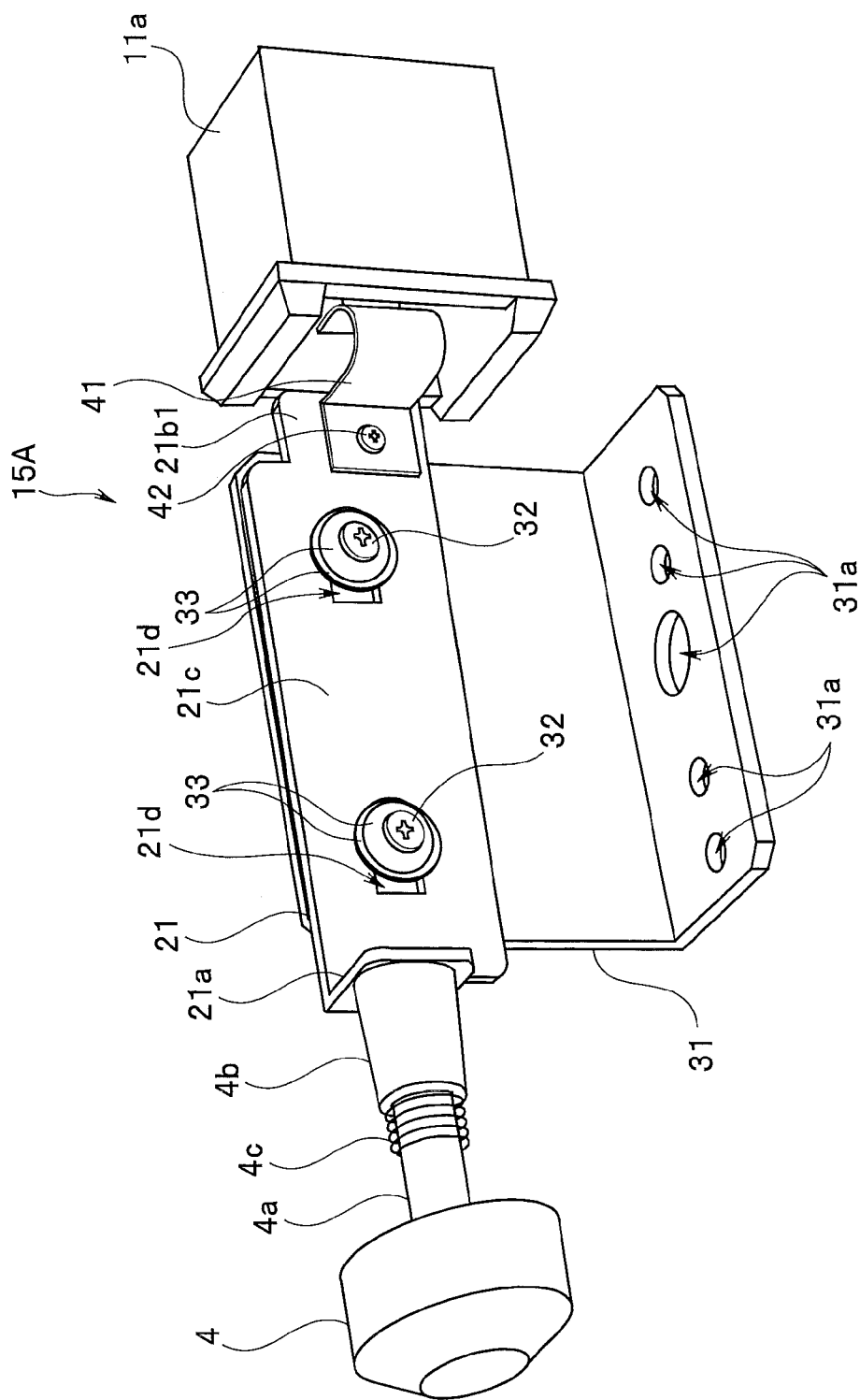
FIG. 9 is a perspective view of the link mechanism 15A when an internal power-supply switch 11a is turned on as a result of a main power-supply button 4 being pressed, according to the second embodiment.
Figure 10:
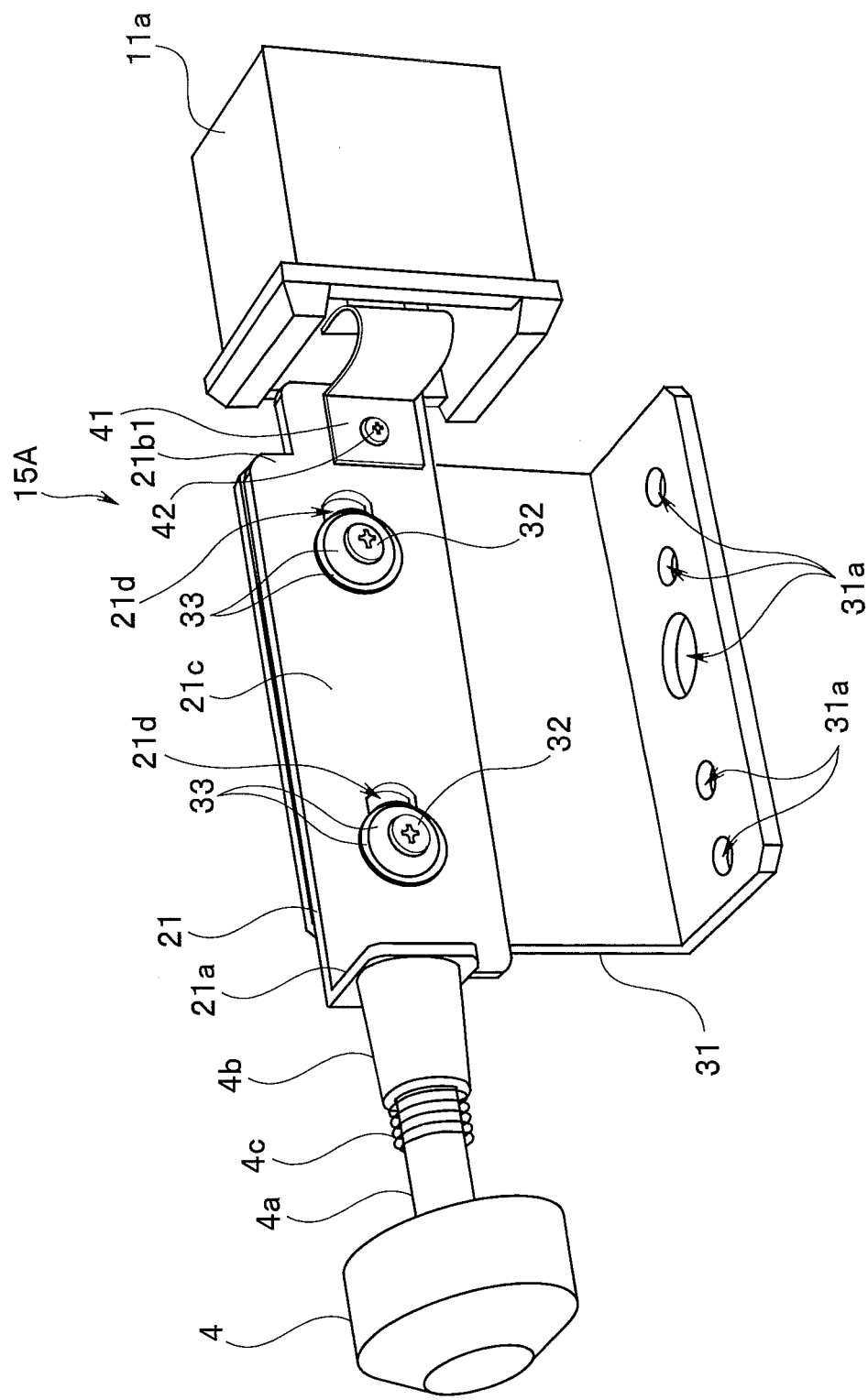
FIG. 10 is a perspective view of the link mechanism 15A when an excessively-large force applied to the main power-supply button 4 is buffered, according to the second embodiment.

FIG. 7 is a conceptual diagram for describing motion of a link mechanism 15A according to the present embodiment. FIG. 8 is a perspective view of the link mechanism 15A. FIG. 8 illustrates an initial state in which a main power-supply button 4 is not pressed. FIG. 9 is a perspective view of the link mechanism 15A when an internal power-supply switch 11a is turned on as a result of the main power-supply button 4 being pressed. FIG. 10 is a perspective view of the link mechanism 15A when an excessively-large force applied to the main power-supply button 4 is buffered.

Note that in FIGS. 8 to 10, a proximal end portion 21b1 of a depressing member 21 is not flexed, and the distal end side of a plate spring 41 is flexed and fixed to the proximal end portion 21b1 of the depressing member 21 via a screw 42.

In the present embodiment, the link mechanism 15A includes the depressing member 21 and the plate spring 41. A proximal end portion of the plate spring 41, which serves as a biasing member, has a U-shape. One end of the plate spring 41 is threadably fastened to the depressing member 21 via the screw 42, and the U-shaped other end is in contact with an operating element 11a1 of an internal power-supply switch 11a. The plate spring 41 is a biasing member having a predetermined amount of biasing force.

The plate spring 41 provides operation of both the moving member 22 and the compression coil spring 23 of the first embodiment. The plate spring 41 is a moving member used in an elastic region. A proximal end portion of the plate spring 41 is a part that is in contact with the internal power-supply switch 11a. Operation of the link mechanism 15A of the present embodiment is the same as that of the link mechanism 15 of the first embodiment.

Upon the depressing member 21 moving toward the inside of the housing 2 beyond the aforementioned predetermined amount of distance d, the plate spring 41 in the link mechanism 15A is compressed so as to absorb the excessive movement amount, whereby breakage of the internal power-supply switch 11a is prevented. As illustrated in FIG. 10, the plate spring 41 provides a movement amount adjusting mechanism that upon depression of the main power-supply button 4, if an amount of movement of the main power-supply button 4 exceeds a predetermined movement amount d, adjusts an amount of movement of a contact portion of the plate spring 41, the contact portion being in contact with the operating element 11a1 of the internal power-supply switch 11a, so that the contact portion becomes smaller relative to the amount of movement of the main power-supply button 4. In other words, upon a movement amount L3 of the main power-supply button 4 exceeding a predetermined amount, the plate spring 41 is compressed against the biasing force of the plate spring 41, whereby the amount of movement of the contact portion of the plate spring 41, the contact portion being in contact with the operating element 11a1 is adjusted.

In other words, during variation from state Sb to state Sc, the plate spring 41 is compressed in an axial direction. As illustrated in FIG. 7, where d1 is a length from a proximal end face of a flexed portion 21b of the depressing member 21 to a proximal end face of a spring receiving portion 22b of a moving member 22 in state Sa and d2 is a length from the proximal end face of the flexed portion 21b of the depressing member 21 to the proximal end face of the spring receiving portion 22b of the moving member 22 in state Sc, a compression amount L2 of the plate spring 41 is expressed by Expression (2) indicated above.

Then, where L1 is a permissible movement amount of the operating element 11a1 of the internal power-supply switch 11a, L2 is an amount of compression of the plate spring 41, which is an amount of adjustment of movement, and L3 is an amount of movement of the main power-supply button 4, as a result of L1, L2 and L3 satisfying Expression (3) above, the internal power-supply switch 11a is prevented from breaking when the main power-supply button 4 is pressed.

Therefore, even upon movement of the main power-supply button 4 causing the internal power-supply switch 11a to move by the permissible movement amount L1 or more as a result of application of an impact force to the main power-supply button 4, the amount of force applied to the main power-supply button 4 is buffered by the plate spring 41 in the link mechanism 15A. As a result, the internal power-supply switch 11a is prevented from being subject to an amount of force exceeding the permissible force amount P3, whereby the internal power-supply switch 11a is prevented from breakage.

As described above, the present embodiment enables provision of a medical apparatus capable of preventing breakage of a power-supply button of an internal power-supply section even if an excessive external force is applied to a power-supply button provided at a housing of the medical apparatus.

Note that in the above description, the plate spring 41 is used in the elastic region; however, the plate spring 41 may be used in a state that allows permanent deformation as long as the internal power-supply switch 11a can be protected from breakage.

Third Embodiment

Although in the first embodiment, in order to prevent the internal power-supply switch 11a from being subject to an amount of force exceeding the permissible force amount P3, the link mechanism uses the compression coil spring 23, in the present embodiment, a link mechanism uses a torsion coil spring.

In the below description, components that are the same as those of the first and second embodiments are provided with reference numerals that are the same as those of the first and second embodiments, and description of such components will be omitted.

Figure 11:
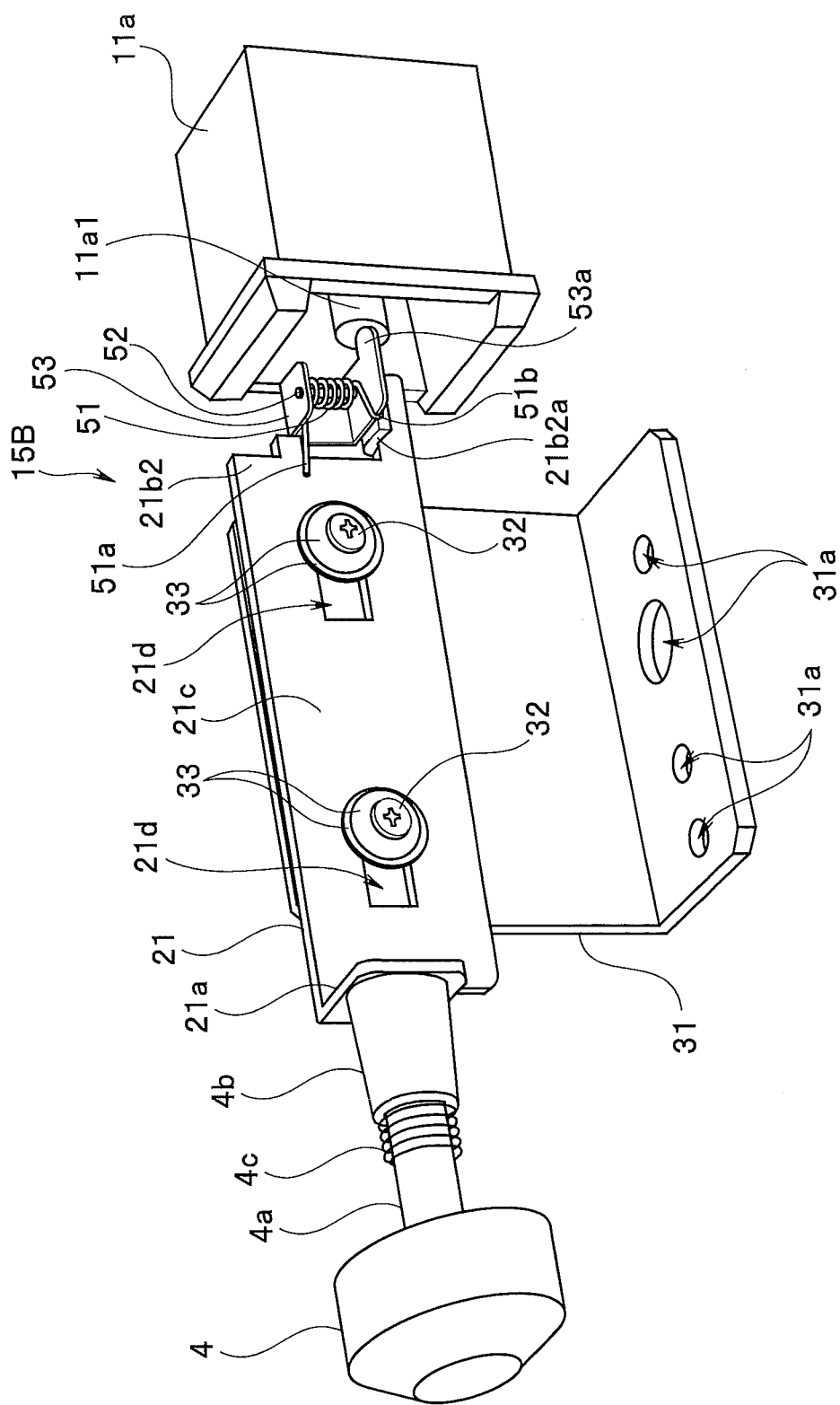
FIG. 11 is a perspective view of a link mechanism 15B according to a third embodiment.
Figure 12:
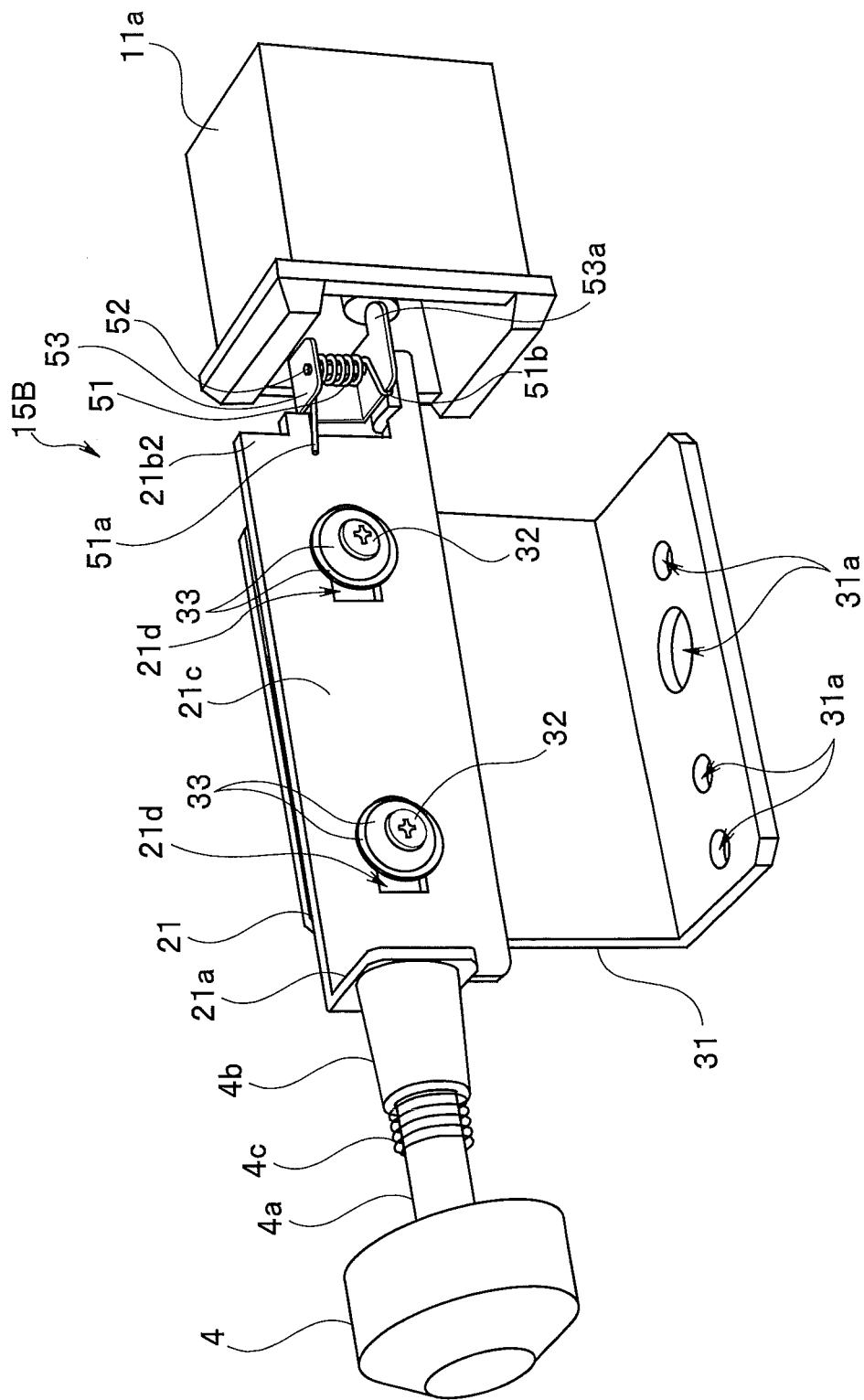
FIG. 12 is a perspective view of the link mechanism 15B when an internal power-supply switch 11a is turned on as a result of a main power-supply button 4 being pressed, according to the third embodiment.

FIG. 11 is a perspective view of a link mechanism 15B according to the present embodiment. FIG. 11 illustrates an initial state in which the main power-supply button 4 is not pressed. FIG. 12 is a perspective view of the link mechanism 15B when the internal power-supply switch 11a is turned on as a result of the main power-supply button 4 being pressed.

Figure 13:
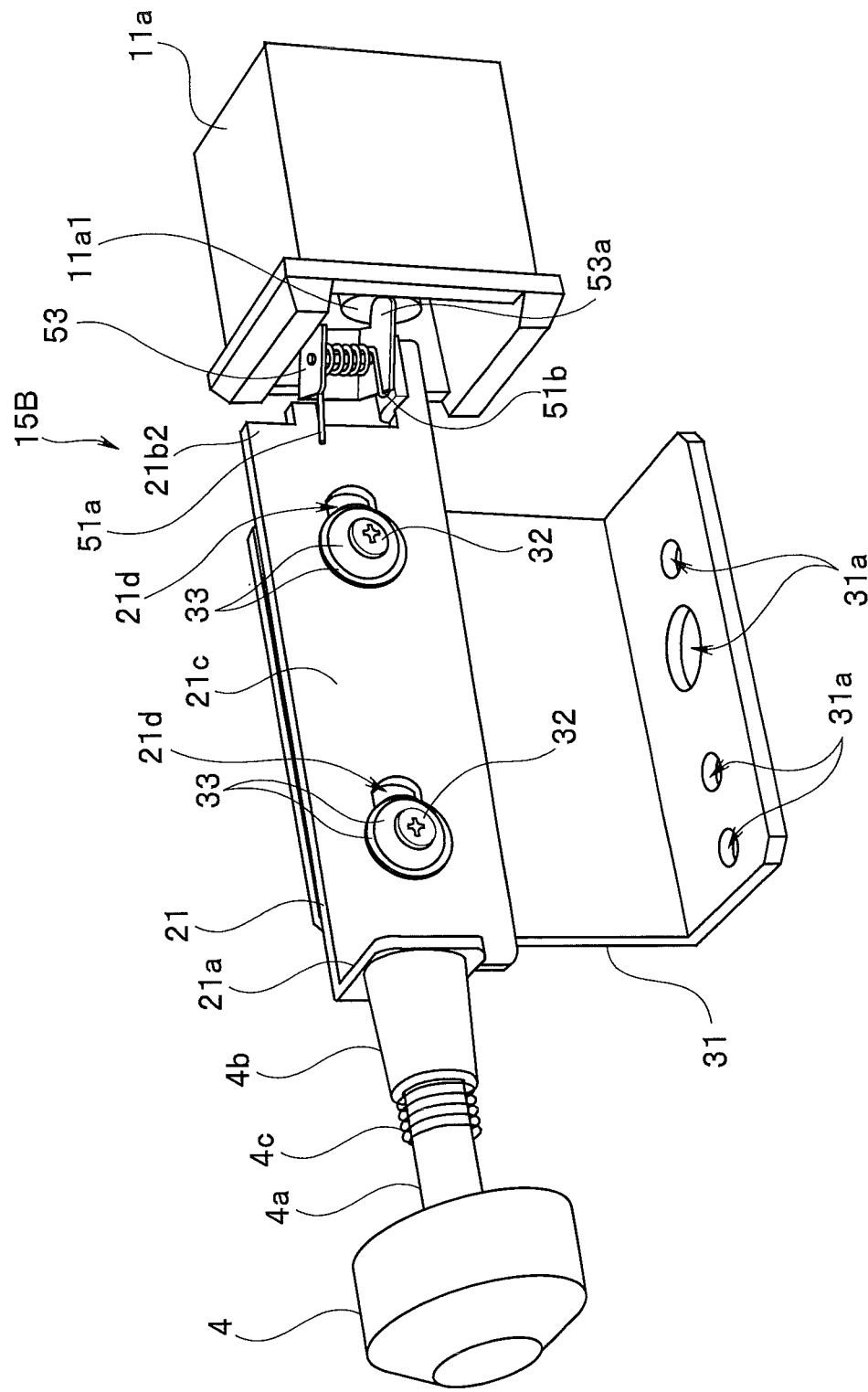
FIG. 13 is a perspective view of the link mechanism 15B when an excessively-large force applied to the main power-supply button 4 is buffered, according to the third embodiment.

FIG. 13 is a perspective view of the link mechanism 15B when an excessively-large force applied to the main power-supply button 4 is buffered.

In the present embodiment, the link mechanism 15B includes a depressing member 21, a torsion coil spring 51 and a pivoting member 53. A metal shaft member 52 fixed to a proximal end portion 21b2 of a depressing member 21 is inserted through the inside of the torsion coil spring 51. The torsion coil spring 51 is a biasing member having a predetermined amount of biasing force. As illustrated in FIG. 11, a part of the proximal end portion of the depressing member 21 is flexed, and the shaft member 52 is fixed to the flexed portion 21b2a in such a manner that an axial direction of the shaft member 52 is perpendicular to a direction in which the main power-supply button 4 is pushed in.

The shaft member 52 is provided with a pivoting member 53 in such a manner that the pivoting member 53 is pivotable about the axis of the shaft member 52. The pivoting member 53 is a metal member formed by a plate-like member being flexed into a square-U shape. The pivoting member 53 includes a projection portion 53a having a semi-circular shape on the distal end side. The projection portion 53a is a part that is in contact with an operating element 11a1. The pivoting member 53 is a moving member provided so as to be pivotable about the axis of the shaft member 52.

One arm portion 51a of the torsion coil spring 51 is in contact with the depressing member 21. The other arm portion 51b of the torsion coil spring 51 engages with one end of the pivoting member 53. Therefore, the respective members of the link mechanism 15B are disposed so that when the main power-supply button 4 is not pressed, a distal end portion of the projection portion 53a is in contact with the operating element 11a1 of the internal power-supply switch 11a. The torsion coil spring 51, which serves as a biasing member, provides operation that is similar to that of the compression coil spring 23 of the first embodiment. Operation of the link mechanism 15B of the present embodiment is the same as the operation of the link mechanism 15 of the first embodiment.

In other words, upon the depressing member 21 moving toward the inside of the housing 2 beyond the aforementioned predetermined amount of distance d, the torsion coil spring 51 in the link mechanism 15B is compressed so as to receive bending stress and the excessive movement amount is absorbed by pivoting of the pivoting member 53, whereby the internal power-supply switch 11a is prevented from breakage.

More specifically, as illustrated in FIG. 12, during movement of the depressing member 21 by the aforementioned predetermined amount of distance d, since the arm portion 51b of the torsion coil spring 51 engages with the pivoting member 53, the distal end portion of the projection portion 53a presses the operating element 11a1 of the internal power-supply switch 11a.

However, even upon movement of the main power-supply button 4 causing the internal power-supply switch 11a to move by the permissible movement amount L1 or more as a result of application of an impact force to the main power-supply button 4, the amount of force applied to the main power-supply button 4 is buffered by the torsion coil spring 51 in the link mechanism 15B. In other words, as illustrated in FIG. 13, upon movement of the main power-supply button 4 causing the internal power-supply switch 11a to move by the permissible movement amount L1 or more, the projection portion 53a receives a depressing force from the operating element 11a1 and the torsion coil spring 51 receives bending moment.

The torsion coil spring 51 and the pivoting member 53 jointly provide a movement amount adjusting mechanism, and upon an amount of movement of the main power-supply button 4 exceeding a predetermined amount, the torsion coil spring 51 is twisted against the biasing force, whereby an amount of movement of a contact portion of the pivoting member 53, which serves as a moving member, the contact portion being in contact with the operating element 11a1, is adjusted. In other words, upon a movement amount L3 of the main power-supply button 4 exceeding a predetermined amount, the torsion coil spring 51 is twisted against the biasing force of the torsion coil spring 51, whereby the amount of movement of the contact portion of the moving member 22 is adjusted.

In other words, during variation from state Sb to state Sc illustrated in FIGS. 3 and 7 in the first and second embodiments, the torsion coil spring 51 is twisted. Where d1 is a length from a proximal end face of the proximal end portion 21b2 of the depressing member 21 to a proximal end portion of the projection portion 53a in state Sa illustrated in FIGS. 3 and 7 and d2 is the length from the proximal end face of the proximal end portion 21b2 of the depressing member 21 to the proximal end portion of the projection portion 53a in state Sc, an amount of contraction of the length from the proximal end face of the proximal end portion 21b2 of the depressing member 21 to the proximal end portion of the projection portion 53a is expressed by L2 in Expression (2) indicated above.

Then, where L1 is a permissible movement amount of the operating element 11a1 of the internal power-supply switch 11a, L2 is an amount of contraction of the length from the proximal end face of the proximal end portion 21b2 of the depressing member 21 to the proximal end portion of the projection portion 53a (movement adjustment amount) and L3 is an amount of movement of the main power-supply button 4, as a result of L1, L2 and L3 satisfying Expression (3) above, the internal power-supply switch 11a is prevented from breakage when the main power-supply button 4 is pressed.

Therefore, as a result of the torsion coil spring 51 receiving the bending moment, the pivoting member 53 pivots, and as a result, internal power-supply switch 11a is prevented from being subject to an amount of force exceeding the permissible force amount P3, whereby the internal power-supply switch 11a is prevented from breakage.

As described above, the present embodiment enables provision of a medical apparatus capable of preventing breakage of a power-supply button of an internal power-supply section even if an excessive external force is applied to a power-supply button provided at a housing of the medical apparatus.

Fourth Embodiment

Although in the first embodiment, in order to prevent the internal power-supply switch 11a from being subject to an amount of force exceeding the permissible force amount P3, the link mechanism uses the compression coil spring 23, in the present embodiment, a link mechanism uses an extension spring.

In the below description, components that are the same as those of the first to third embodiments are provided with reference numerals that are the same as those of the first to third embodiments, and description of such components will be omitted.

Figure 14:
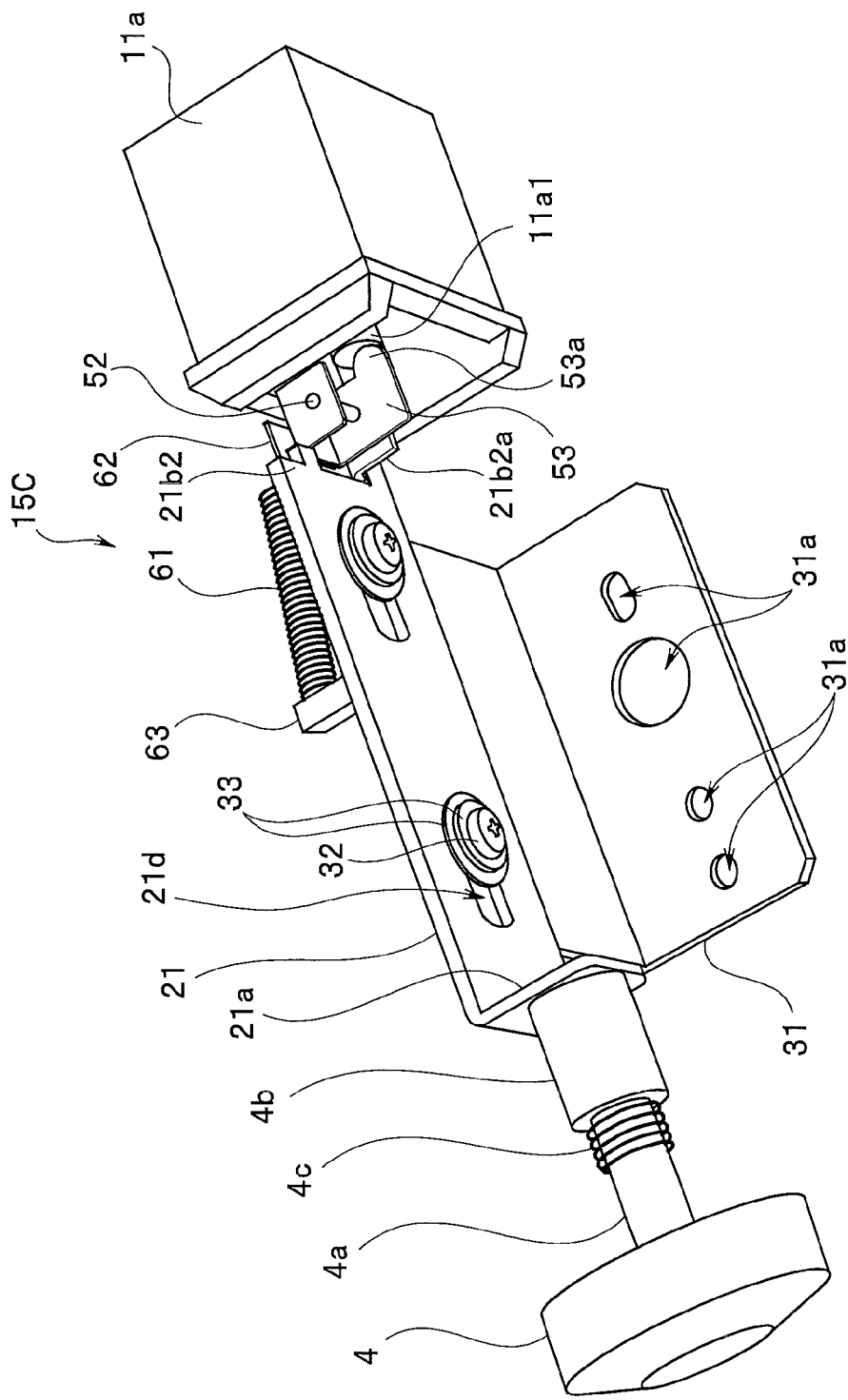
FIG. 14 is a perspective view of a link mechanism 15C according to a fourth embodiment.
Figure 15:
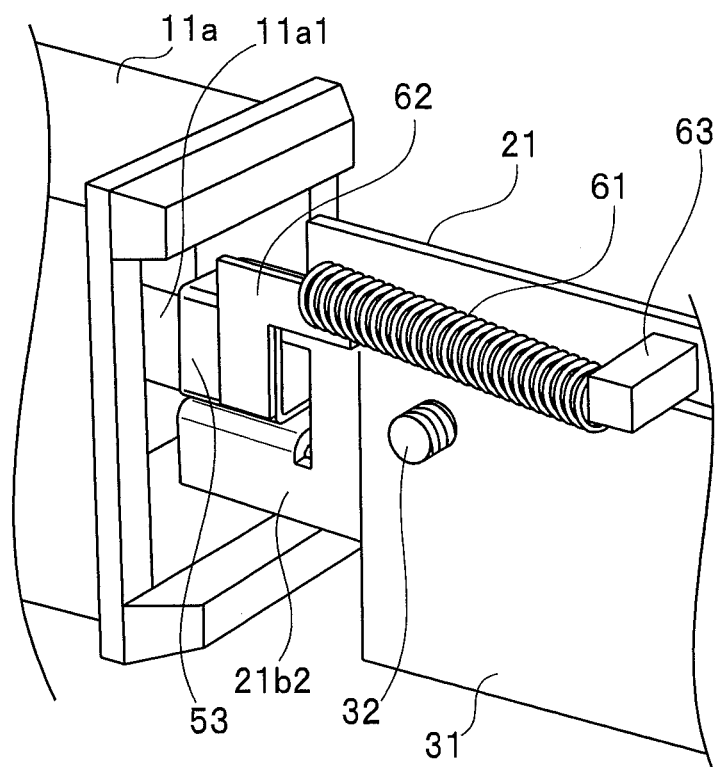
FIG. 15 is a perspective view of a part of the link mechanism 15C as viewed from a viewpoint that is different from that in FIG. 14.
Figure 16:
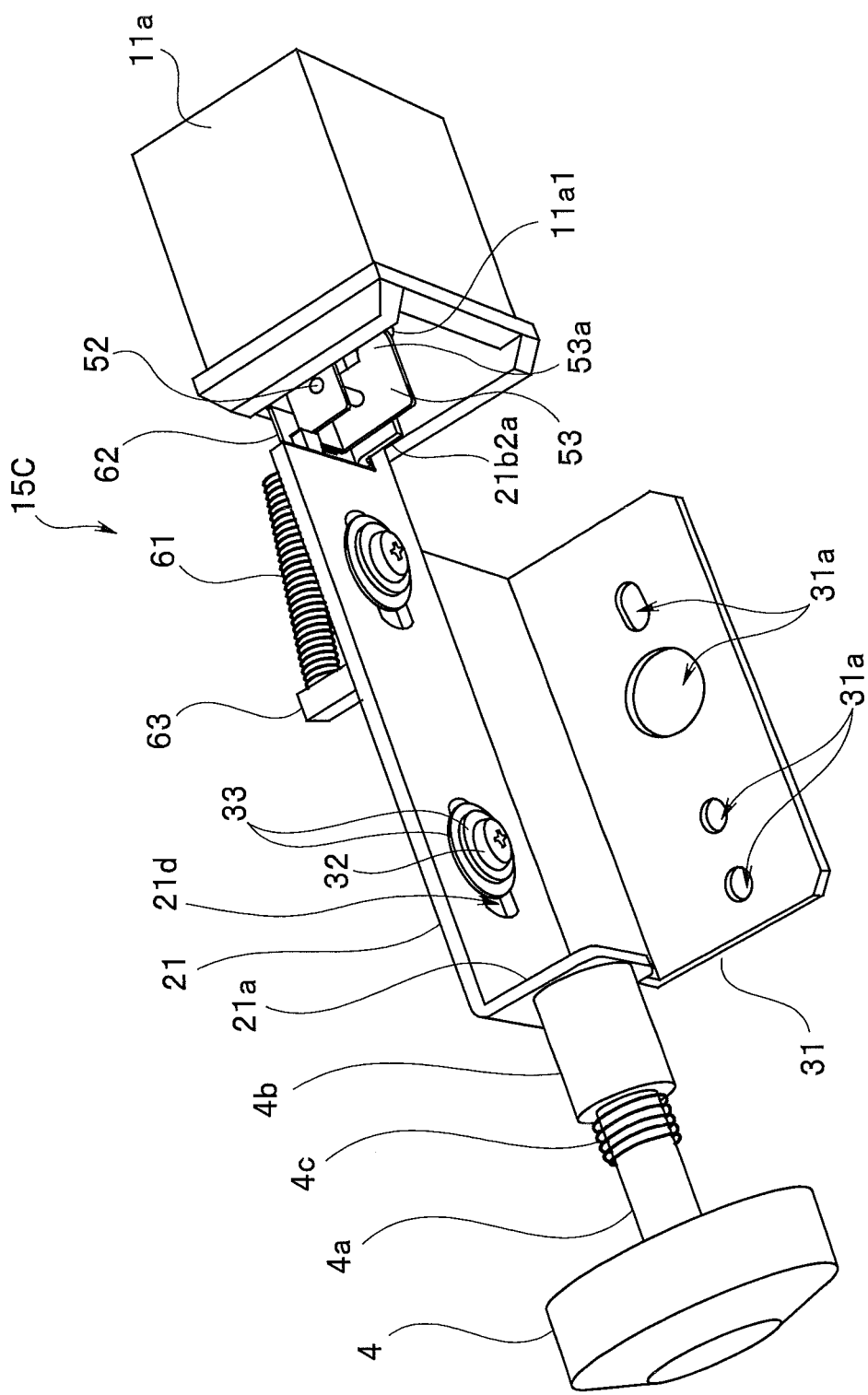
FIG. 16 is a perspective view of the link mechanism 15C when an internal power-supply switch 11a is turned on as a result of a main power-supply button 4 being pressed, according to the fourth embodiment.
Figure 17:
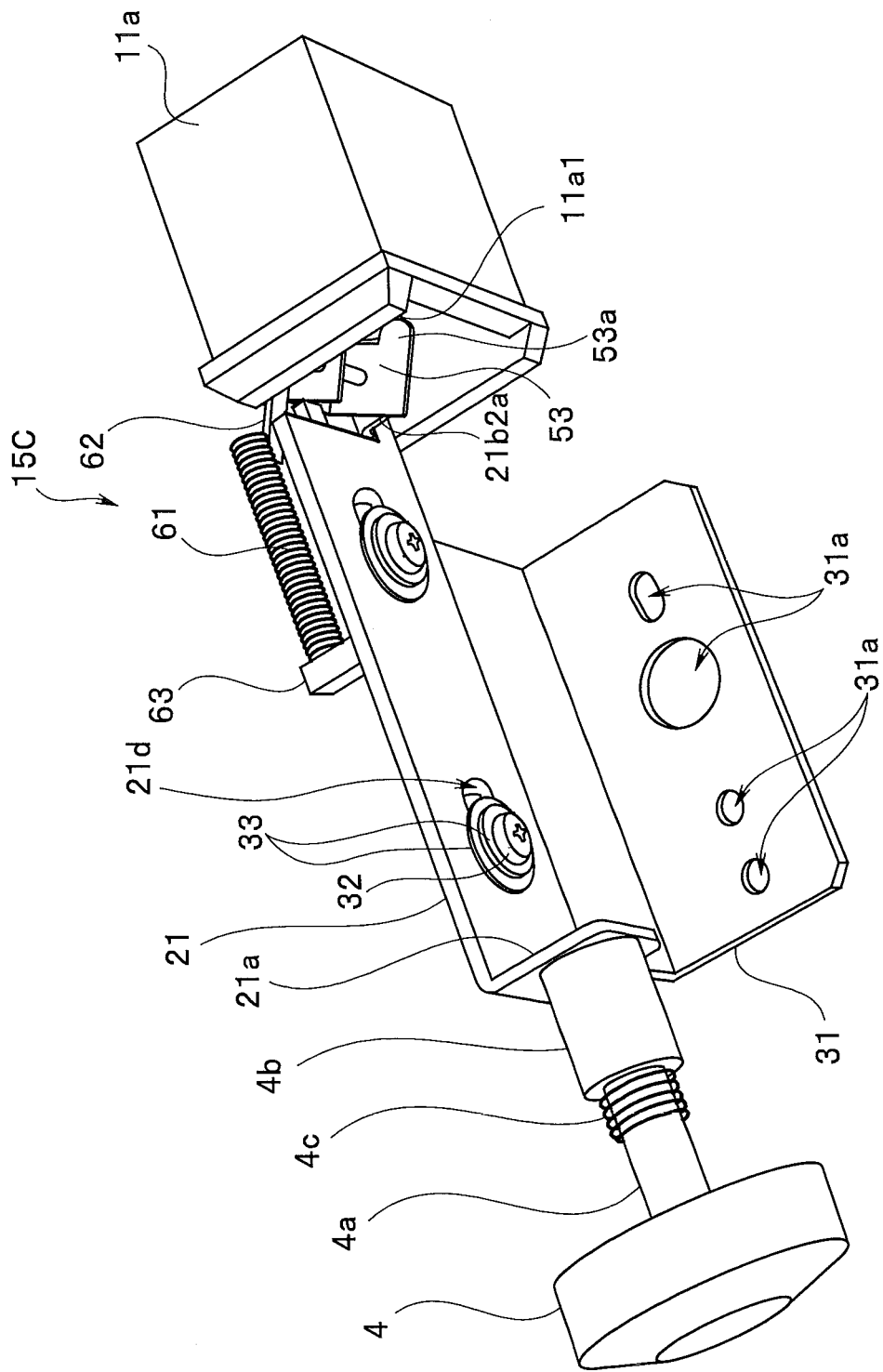
FIG. 17 is a perspective view of the link mechanism 15C when an excessively-large force applied to the main power-supply button 4 is buffered, according to the fourth embodiment.

FIG. 14 is a perspective view of a link mechanism 15C according to the present embodiment. FIG. 14 illustrates an initial state in which the main power-supply button 4 is not pressed. FIG. 15 is a perspective view of a part of the link mechanism 15C as viewed from a viewpoint that is different from that in FIG. 14. FIG. 16 is a perspective view of the link mechanism 15C when an internal power-supply switch 11a is turned on as a result of a main power-supply button 4 being pressed. FIG. 17 is a perspective view of the link mechanism 15C when an excessively-large force applied to the main power-supply button 4 is buffered.

In the present embodiment, the link mechanism 15C includes a depressing member 21, an extension spring 61 and a pivoting member 53. One end of the extension spring 61 engages with and is fixed to a fixed member 62 fixed to a pivoting member 53, and the other end of the extension spring 61 engages with and is fixed to a fixed member 63 fixed to the depressing member 21.

As illustrated in FIGS. 14 and 15, at an initial position where the main power-supply button 4 is not pressed, the extension spring 61 pulls the fixed member 62 fixed to the pivoting member 53 to the distal end side. At this time, a projection portion 53a of the pivoting member 53 is in contact with an operating element 11a1, but respective members of the link mechanism 15C are disposed so that the projection portion 53a does not push the internal power-supply switch 11a in. The extension spring 61, which serves as a biasing member, provides operation that is similar to that of the torsion coil spring 51 of the third embodiment. Operation of the link mechanism 15C of the present embodiment is the same as the operation of the link mechanism 15 of the first embodiment.

In other words, upon the depressing member 21 moving toward the inside of the housing 2 beyond the aforementioned predetermined amount of distance d, the pivoting member 53 pivots about an axis of the shaft member 52 against a biasing force of the extension spring 61 so as to absorb the excessive movement amount, whereby the internal power-supply switch 11a is prevented from breakage.

More specifically, as illustrated in FIG. 16, during movement of the depressing member 21 by the aforementioned predetermined amount of distance d, the extension spring 61 pulls the fixed member 62 fixed to the pivoting member 53, and thus a distal end portion of the projection portion 53a presses the operating element 11a1 of the internal power-supply switch 11a.

However, even upon movement of the main power-supply button 4 causing the internal power-supply switch 11a to move by a permissible movement amount L1 or more as a result of application of an impact force to the main power-supply button 4, the amount of force applied to the main power-supply button 4 is buffered by the extension spring 61 in the link mechanism 15C. In other words, the extension spring 61 and the pivoting member 53 jointly provide a movement amount adjusting mechanism, and upon a movement amount L3 of the main power-supply button 4 exceeding a predetermined amount, the extension spring 61 is pulled against the biasing force, whereby an amount of movement of a contact portion of the pivoting member 53, which is a moving member, the contact portion being in contact with the operating element 11a1, is adjusted.

In other words, during variation from state Sb to state Sc in FIGS. 3 and 7 in the first and second embodiments, the extension spring 61 is pulled. Where d1 is a length from a proximal end face of a proximal end portion 21b2 of the depressing member 21 to a proximal end portion of the projection portion 53a in state Sa illustrated in FIGS. 3 and 7 and d2 is the length from the proximal end face of the proximal end portion 21b2 of the depressing member 21 to the proximal end portion of the projection portion 53a in state Sc, an amount of contraction of the length from the proximal end face of the proximal end portion 21b2 of the depressing member 21 to the proximal end portion of the projection portion 53a is expressed by L2 in Expression (2) above.

Then, where L1 is a permissible movement amount of the operating element 11a1 of the internal power-supply switch 11a, L2 is an amount of contraction of the length from the proximal end face of the proximal end portion 21b2 of the depressing member 21 to the proximal end portion of the projection portion 53a (movement adjustment amount) and L3 is an amount of movement of the main power-supply button 4, as a result of L1, L2 and L3 satisfying Expression (3) above, the internal power-supply switch 11a is prevented from breakage when the main power-supply button 4 is pressed.

As illustrated in FIG. 17, upon movement of the main power-supply button 4 causing the internal power-supply switch 11a to move by the permissible movement amount L1 or more, the projection portion 53a receives a depressing force from the operating element 11a1 and the extension spring 61 receives tension stress. As a result of the extension spring 61 receiving the tension stress, the pivoting member 53 pivots, and as a result, the internal power-supply switch 11a is prevented from being subject to an amount of force exceeding the permissible force amount P3, whereby the internal power-supply switch 11a is prevented from breakage.

As described above, the present embodiment enables provision of a medical apparatus capable of preventing breakage of a power-supply button of an internal power-supply section even if an excessive external force is applied to a power-supply button provided at a housing of the medical apparatus.

Note that although in each of the above-described embodiments, an elastic member such as a compression coil spring 23 or a plate spring 41 is disposed on the proximal end side of the depressing member 21, the elastic member may be disposed on the distal end side of the depressing member 21 or between divided depressing members.

Next, modifications of the four embodiments described above will be described. Note that here, although each modification will be described in terms of an example of the main power-supply button 4 and the link mechanism 15 indicated in the first embodiment, each of the below-described modifications is applicable also to the second to fourth embodiments.

(Modification 1)

The present modification relates to a configuration in which a protection member is provided on a main power-supply button 4 to restrict an amount of movement of the main power-supply button 4, whereby an impact force applied to the internal power-supply switch 11a is relaxed.

Figure 18:
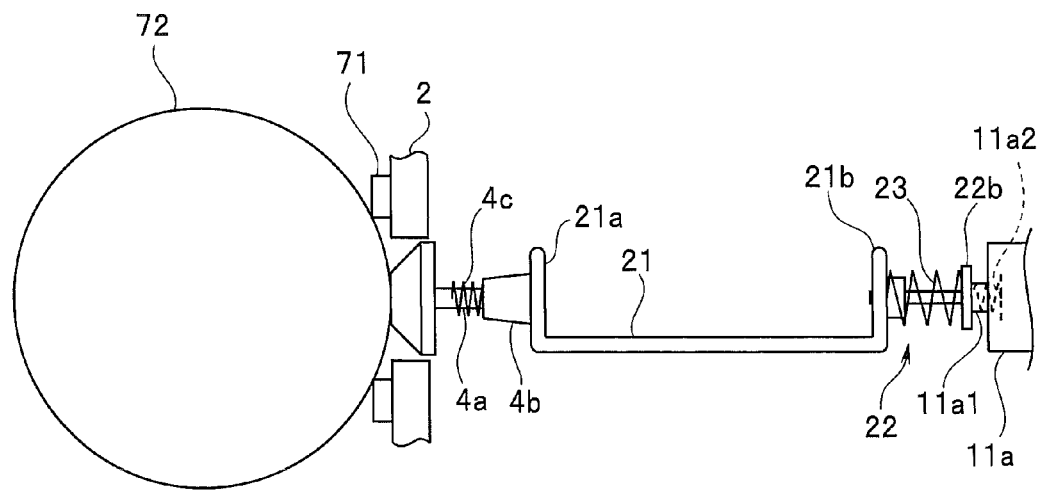
FIG. 18 is a diagram of a configuration of a link mechanism 15 in a housing 2 of an ultrasound observation apparatus 1 according to modification 1.

FIG. 18 is a diagram of a configuration of a link mechanism 15 in a housing 2 of an ultrasound observation apparatus 1 according to modification 1. A protection member 71 is provided on a surface of a housing 2 so as to surround a periphery of the main power-supply button 4 having a round shape as viewed from the front. The protection member 71 is, for example, an annular member. An inner diameter and a thickness (that is, a height from an outer surface of the housing 2) of the protection member 71 are, for example, an inner diameter and a thickness that provide an amount of movement of the main power-supply button 4, the amount being the aforementioned predetermined amount d or less, when a hard ball 72 collides with the main power-supply button 4 in a hard ball dropping test prescribed in standards or the like. Note that the protection member 71 may be a part of the housing 2, the part being formed so as to project from the outer surface.

In other words, the protection member 71 is a projection portion provided in the vicinity of the main power-supply button 4, the projection portion restricting an amount of movement of the main power-supply button 4 in a direction of depression. Such configuration enables further prevention of breakage of the internal power-supply switch 11a in the ultrasound observation apparatus 1 of each of the above-described embodiments.

Also, the inner diameter and the thickness of the protection member 71 may be ones that may provide an amount of movement of the main power-supply button 4, the amount being the aforementioned predetermined amount d or more when a hard ball 72 collides with the main power-supply button 4 in a hard ball dropping test prescribed in standards or the like.

Figure 19:
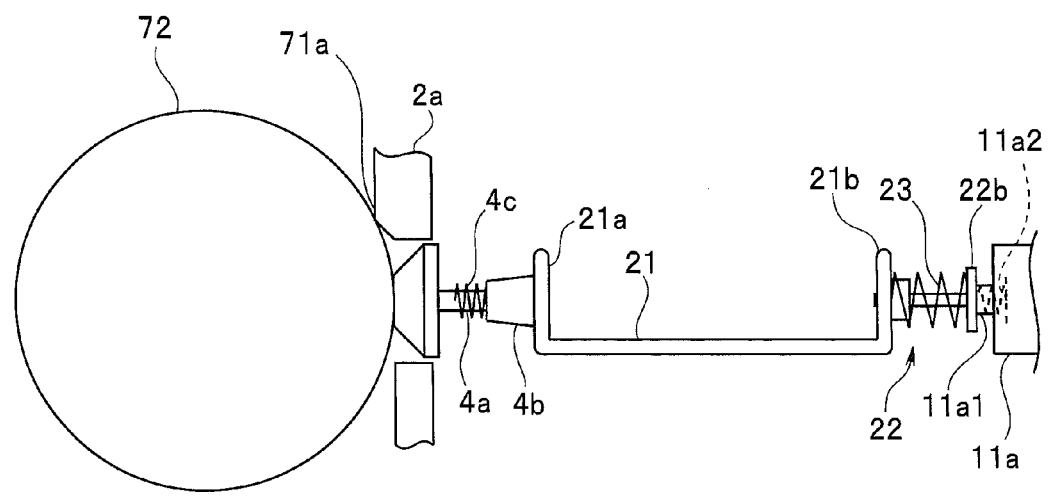
FIG. 19 is a diagram of a configuration of the link mechanism 15 in the housing 2 of the ultrasound observation apparatus 1 where a protection member 71a is formed by a part of the housing 2 so as to surround a part of a periphery of the main power-supply button 4, according to modification 1.

Furthermore, the protection member 71 may be formed so as to surround a part of the periphery of the main power-supply button 4 rather than surrounding the entire periphery of the main power-supply button 4. FIG. 19 is a diagram of a configuration of a link mechanism 15 in a housing 2 of an ultrasound observation apparatus 1 where a protection member 71a is formed by a part of the housing 2 so as to surround a part of a periphery of a main power-supply button 4.

Therefore, the present modification enables relaxation of an impact force applied to the internal power-supply switch 11a.

Note that each of the protection member 71 and 71a does not need to be one that buffers 100% of, e.g., an impact force of a hard ball 72 when the hard ball 72 collides with the main power-supply button 4 in a hard ball dropping test prescribed in standards or the like, and may be one including a configuration or a material that allows the relevant protection member to be destroyed as long as such configuration or material can, for example, prolong a duration of exertion of an impact force at the time of a collision.

(Modification 2)

The present modification relates to a configuration in which a locking member is provided at a position partway through a pathway of movement of a depressing member 21 to restrict an amount of movement of the depressing member 21, whereby an impact force applied to an internal power-supply switch 11a is relaxed.

Figure 20:
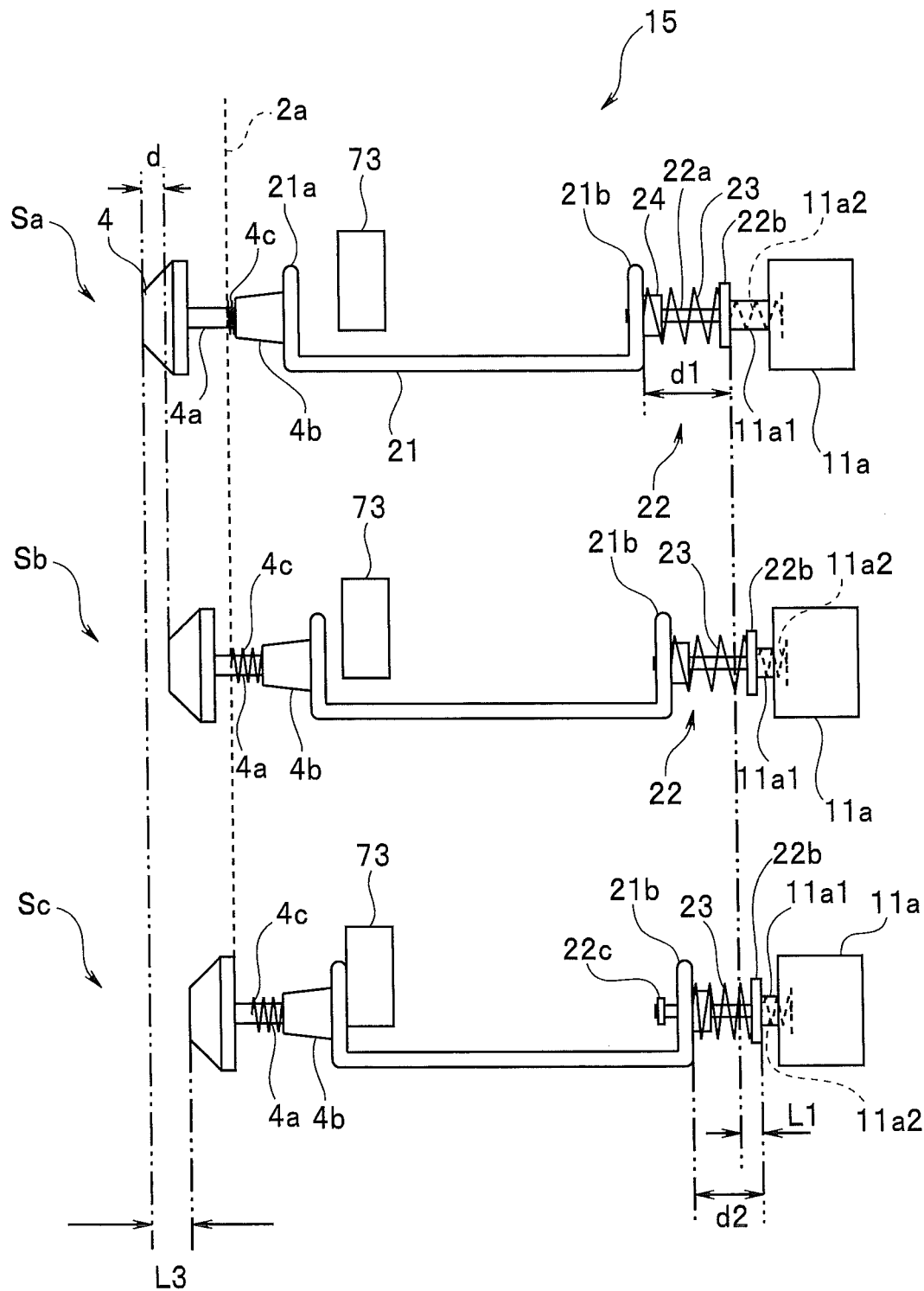
FIG. 20 is a conceptual diagram for describing motion of a link mechanism in a housing 2 of an ultrasound observation apparatus 1 according to modification 2.

FIG. 20 is a conceptual diagram for describing motion of a link mechanism in a housing 2 of an ultrasound observation apparatus 1 according to modification 2.

A locking member 73, which is a member fixed to the housing 2, is disposed at a position where the locking member 73 is not in contact with a depressing member 21 when an operation to turn a main power-supply button 4 on/off is performed but is brought into contact with the depressing member 21 when the main power-supply button 4 is pushed in by a predetermined movement amount d or more. In other words, the locking member 73 is provided inside the ultrasound observation apparatus 1 and restricts an amount of movement of the depressing member 21 in a direction of depression.

Such configuration enables further prevention of breakage of the internal power-supply switch 11a in the ultrasound observation apparatus 1 according to each of the above-described embodiments and modification 1.

As described above, each of the above-described embodiments and modifications enables provision of a medical apparatus capable of preventing breakage of a power-supply button of an internal power-supply section even if an excessive external force is applied to a power-supply button provided at a housing of the medical apparatus.

Note that although each of the embodiments and modifications has been described in terms of an ultrasound observation apparatus as an example of medical apparatuses, the present invention is applicable to medical devices other than ultrasound observation apparatuses.

The present invention is not limited to the above-described embodiments, various modifications, alterations and the like are possible without departing from the spirit of the present invention.

What is claimed is:

1. A medical apparatus including a housing, the medical apparatus comprising:
    a power-supply section disposed in an inside of the medical apparatus;
    a power-supply button provided at an outer face of the housing, the power-supply button operating the power-supply section to be turned on/off as a result of depression of the power-supply button;
    a moving member capable of moving in conjunction with the depression of the power-supply button;
    a switch provided at the power-supply section so as to be in contact with the moving member, the switch switching the power-supply section on/off as a result of the switch being depressed along with movement of the moving member; and
    a movement amount adjusting mechanism that upon the depression of the power-supply button, if an amount of movement of the power-supply button exceeds a predetermined movement amount, adjusts an amount of movement of a contact portion of the moving member, the contact portion being in contact with the switch, so that the amount of movement of the contact portion of the moving member becomes smaller relative to the amount of movement of the power-supply button.

2. The medical apparatus according to claim 1, wherein if L1 is a permissible movement amount of an operating element provided in the depressed switch, L2 is a movement adjustment amount of the moving member and L3 is the amount of movement of the power-supply button upon the depression, the movement amount adjusting mechanism adjusts the amount of movement of the moving member so as to satisfy $L2 \geq L3-L1$.

3. The medical apparatus according to claim 1, wherein the movement amount adjusting mechanism includes a biasing member having a predetermined amount of biasing force, and if the amount of movement of the power-supply button exceeds the predetermined movement amount, the biasing member is compressed against the biasing force, whereby the amount of movement of the moving member is adjusted.

4. The medical apparatus according to claim 3, wherein the biasing member is a compression coil spring.

5. The medical apparatus according to claim 1, wherein the moving member is a biasing member having a predetermined amount of biasing force, and if the amount of movement of the power-supply button exceeds the predetermined movement amount, the biasing member is compressed against the biasing force, whereby the amount of movement of the contact portion of the moving member is adjusted.

6. The medical apparatus according to claim 5, wherein the biasing member is a plate spring.

7. The medical apparatus according to claim 1, wherein the movement amount adjusting mechanism includes a biasing member having a predetermined amount of biasing force, and if the amount of movement of the power-supply button exceeds the predetermined movement amount, the biasing member is twisted against the biasing force, whereby the amount of movement of the contact portion of the moving member is adjusted.

8. The medical apparatus according to claim 7, wherein the biasing member is a torsion coil spring.

9. The medical apparatus according to claim 1, wherein the movement amount adjusting mechanism includes a biasing member having a predetermined amount of biasing force, and if the amount of movement of the power-supply button exceeds the predetermined movement amount, the biasing member is pulled against the biasing force, whereby the amount of movement of the contact portion of the moving member is adjusted.

10. The medical apparatus according to claim 9, wherein the biasing member is an extension coil spring.

11. The medical apparatus according to claim 3, wherein where P1 is a depressing force generated upon the depression of the power-supply button, P2 is the predetermined force amount of biasing member and P3 is a permissible withstanding force of the switch, the biasing member varies a force of depressing the switch so as to satisfy $P3 \geq P1-P2$.

12. The medical apparatus according to claim 1, comprising a depressing member interposed between the power-supply button and the moving member.

13. The medical apparatus according to claim 12, comprising a locking member provided inside the medical apparatus, the locking member restricting an amount of movement of the depressing member in the direction of the depression.

14. The medical apparatus according to claim 1, comprising a projection portion provided in a vicinity of the power-supply button, the projection portion restricting an amount of movement of the power-supply button in the direction of the depression.

15. The medical apparatus according to claim 1, wherein a depressing force generated upon the depression of the power-supply button is no more than 250 N.

* * * * *